US006551319B2

(12) United States Patent
Lieberman

(10) Patent No.: US 6,551,319 B2
(45) Date of Patent: *Apr. 22, 2003

(54) APPARATUS FOR IMPLANTATION INTO BONE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 63 days.

This patent is subject to a terminal disclaimer.

(21) Appl. No.: 09/812,085

(22) Filed: Mar. 19, 2001

(65) Prior Publication Data

US 2002/0055738 A1 May 9, 2002

Related U.S. Application Data

(63) Continuation-in-part of application No. 09/781,847, filed on Feb. 14, 2001, which is a continuation-in-part of application No. 09/708,940, filed on Nov. 8, 2000, and a continuation-in-part of application No. 09/708,292, filed on Nov. 8, 2000, now Pat. No. 6,468,309.

(51) Int. Cl.$^7$ .............................................. A61B 17/56
(52) U.S. Cl. ........................................ 606/61; 606/69
(58) Field of Search ............................ 606/61, 69, 70, 606/71, 72, 73

(56) References Cited

U.S. PATENT DOCUMENTS

| 2,033,039 A | 3/1936 | Limpert ..................... 24/710.9 |
| 4,762,453 A | 8/1988 | DeCaro ....................... 411/383 |
| 4,854,311 A | 8/1989 | Steffee .......................... 606/66 |
| 4,961,740 A | 10/1990 | Ray et al. ...................... 606/61 |
| 5,055,104 A | 10/1991 | Ray .............................. 606/61 |

(List continued on next page.)

FOREIGN PATENT DOCUMENTS

| EP | 0374088 A1 | 6/1990 |
| EP | 0663184 A1 | 7/1995 |
| FR | 2299548 | 8/1976 |
| SU | 1071297 A | 2/1984 |
| WO | WO0224087 A1 | 3/2002 |

OTHER PUBLICATIONS

An article entitled "Anterior Vertebral Body Screw Pullout Testing, A Comparison of Zielke, Kaneda, Universal Spine System, and Universal Spine System with Pullout–Resistant Nut", by Isador H. Lieberman et al., reprinted from Spine, vol. 23, No. 8, Apr. 15, 1998.

An excerpt from *The Application of Shape Memory Alloys in Medicine*; Author: I. P. Lipscomb, 1996; Contents; Forward; Preface; Chapter 1 "Introduction to Shape Memory Alloys (SMAs)".

An excerpt from *The Application of Shape Memory Alloys in Medicine*; Author: I. P. Lipscomb, 1996; Chapter 2 entitled "Characteristics of Shape Memory Alloys in Medical Applications".

An excerpt from *The Application of Shape Memory Alloys in Medicine*; Author: I. P. Lipscomb, 1996; Chapter 5 "Present and Future Orthopaedic Applications".

Primary Examiner—John J. Wilson
(74) Attorney, Agent, or Firm—Tarolli, Sundheim, Covell & Tummino L.L.P.

(57) ABSTRACT

An apparatus (10) is provided for implantation into a bone (12) in a patient's spine or pelvis. The apparatus (10) comprises a platform (24) having a first surface (38) for facing the bone (12). The platform (24) includes structure (32, 34, 36) for connection to a spinal fixation implant (100). The apparatus (10) further comprises helical spikes (50, 52) for embedding into the bone (12) upon rotation of the platform (24). The helical spikes (50, 52) project tangentially from the platform (24) and extend around a longitudinal axis (22). The helical spikes (50, 52) have a tip portion (58) which penetrates into the bone (12) as the platform (24) is rotated. The helical spikes (50, 52), when implanted, have a conical shape that increases in diameter as the helical spikes extend away from the platform (24). The helical spikes (50, 52) may be made from a shape memory alloy.

82 Claims, 15 Drawing Sheets

U.S. PATENT DOCUMENTS

| | | | | |
|---|---|---|---|---|
| 5,246,443 A | * | 9/1993 | Mai | 606/78 |
| 5,263,953 A | | 11/1993 | Bagby | 606/61 |
| 5,290,289 A | | 3/1994 | Sanders et al. | 606/61 |
| 5,534,031 A | | 7/1996 | Matsuzaki et al. | 623/17 |
| 5,582,616 A | | 12/1996 | Bolduc et al. | 606/143 |
| 5,626,613 A | | 5/1997 | Schmieding | 606/232 |
| 5,662,683 A | | 9/1997 | Kay | 606/232 |
| 5,728,116 A | | 3/1998 | Rosenman | 606/151 |
| 5,791,899 A | | 8/1998 | Sachdeva et al. | 433/173 |
| 5,800,550 A | | 9/1998 | Sertich | 606/43 |
| 5,810,851 A | | 9/1998 | Yoon | 606/148 |
| 5,824,008 A | | 10/1998 | Bolduc et al. | 606/43 |
| 5,888,223 A | | 3/1999 | Bray, Jr. | 623/17 |
| 5,904,696 A | | 5/1999 | Rosenman | 606/151 |
| 6,010,502 A | | 1/2000 | Bagby | 606/61 |
| 6,036,701 A | | 3/2000 | Rosenman | 606/151 |
| 6,071,310 A | | 6/2000 | Picha et al. | 623/17 |
| 6,080,155 A | | 6/2000 | Michelson | 606/61 |
| 6,102,950 A | | 8/2000 | Vaccaro | 623/17 |
| 6,106,557 A | | 8/2000 | Robioneck et al. | 623/17 |
| 6,113,638 A | | 9/2000 | Williams et al. | 623/17 |
| 6,120,502 A | | 9/2000 | Michelson | 606/61 |
| 6,120,503 A | | 9/2000 | Michelson | 606/61 |
| 6,123,705 A | | 9/2000 | Michelson | 606/61 |
| 6,126,688 A | | 10/2000 | McDonnell | 623/17.16 |
| 6,126,689 A | | 10/2000 | Brett | 623/17.16 |
| 6,206,882 B1 | * | 3/2001 | Cohen | 606/69 |
| 6,296,656 B1 | | 10/2001 | Bolduc et al. | 606/213 |

* cited by examiner

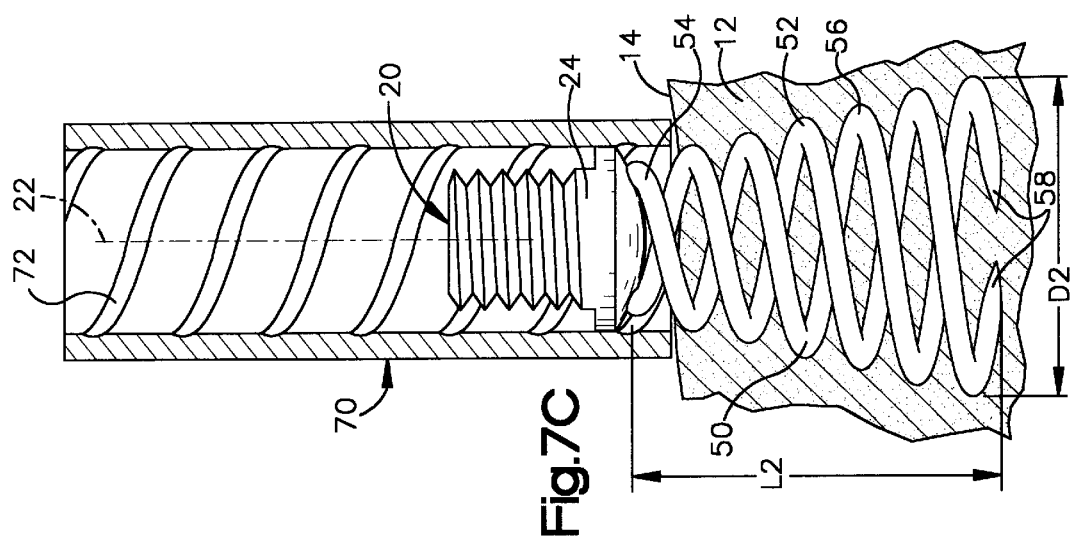
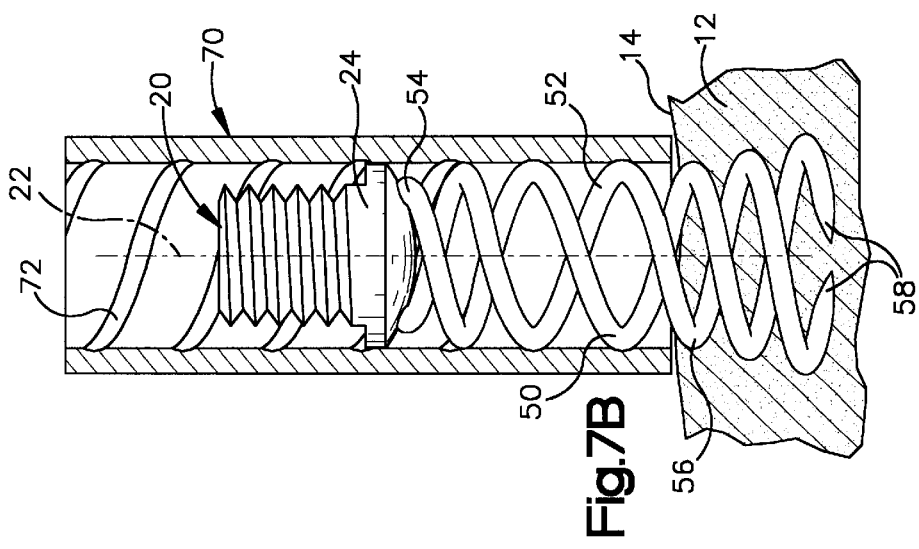
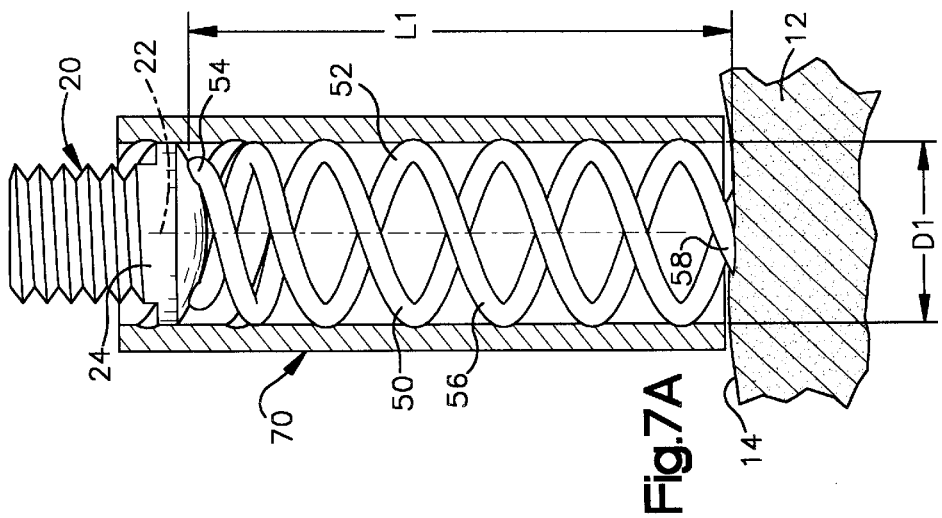

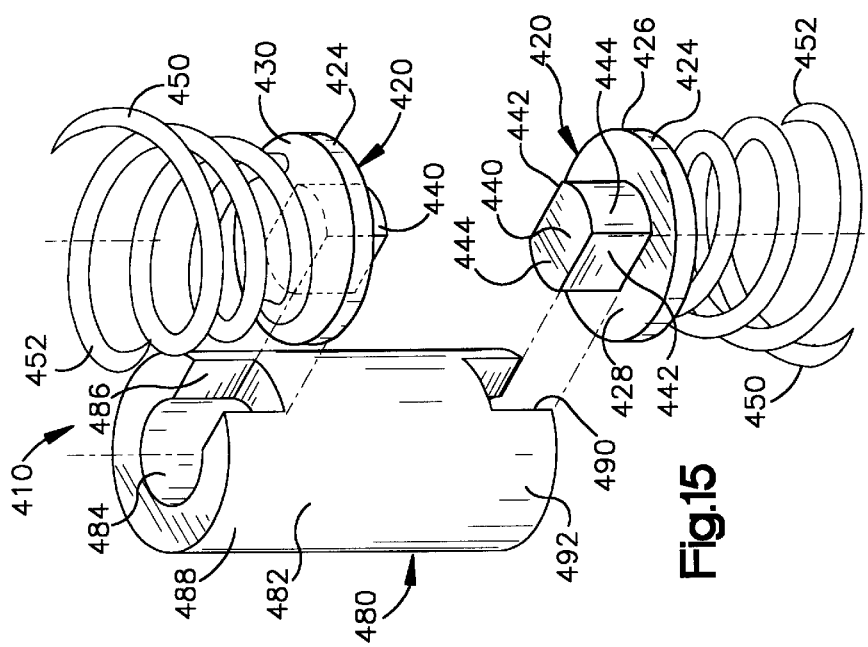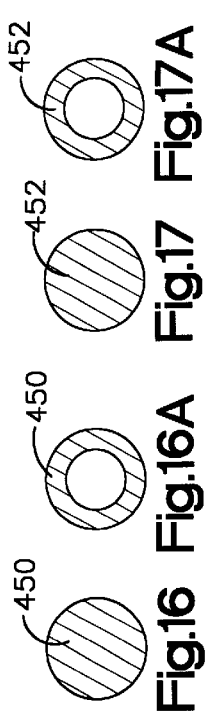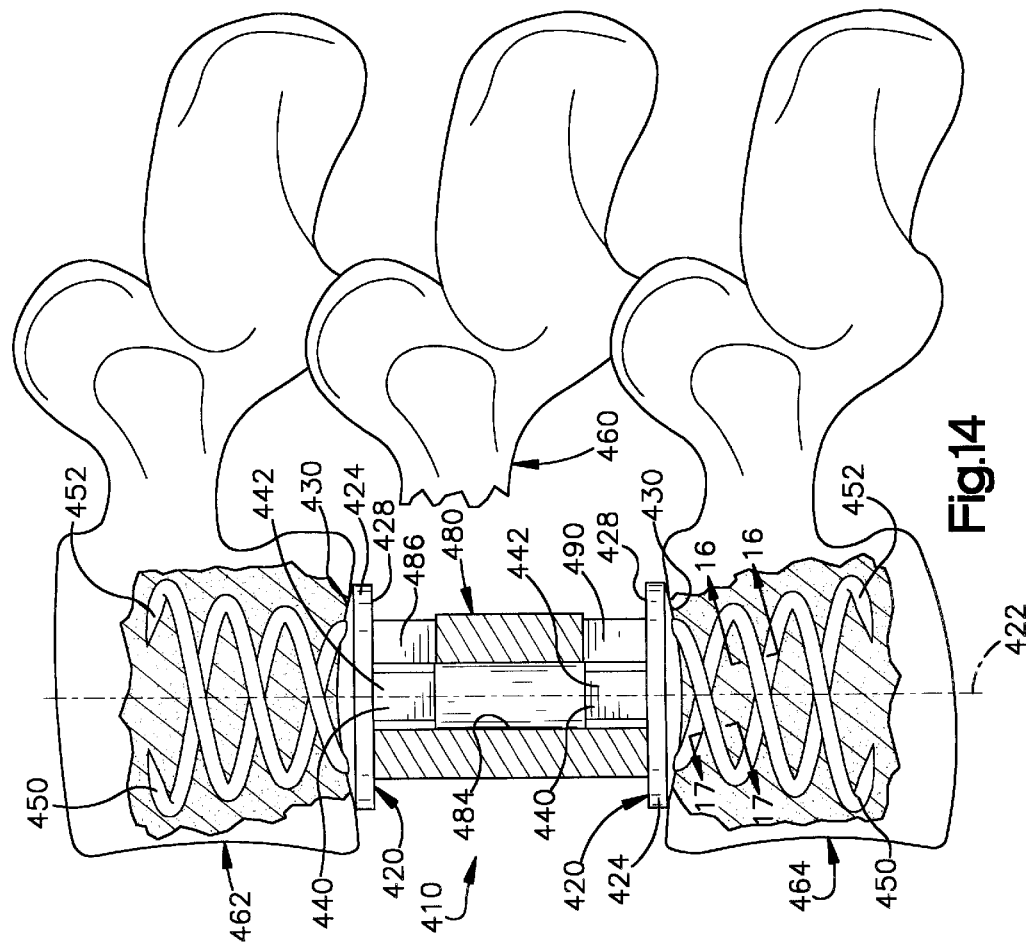

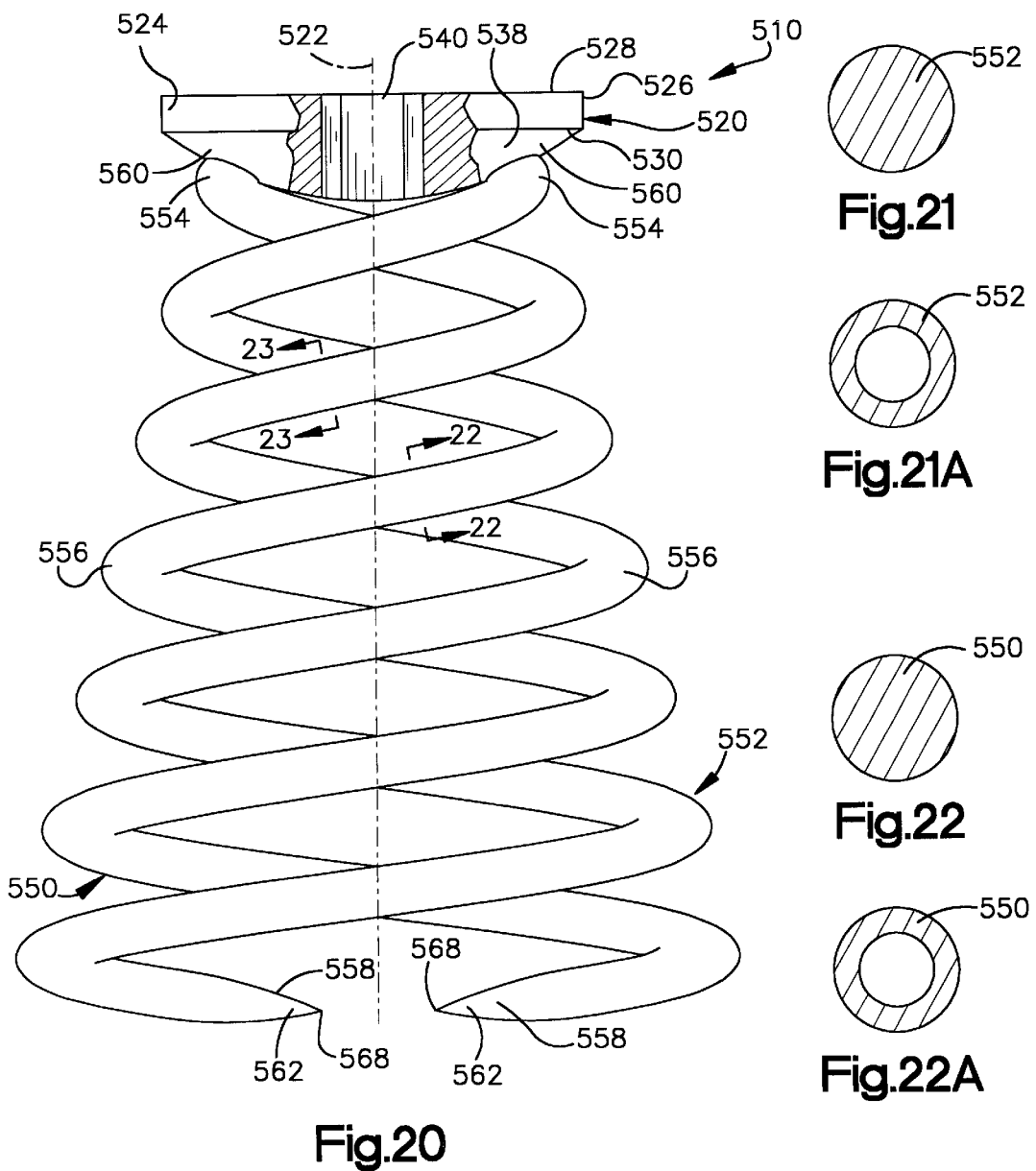

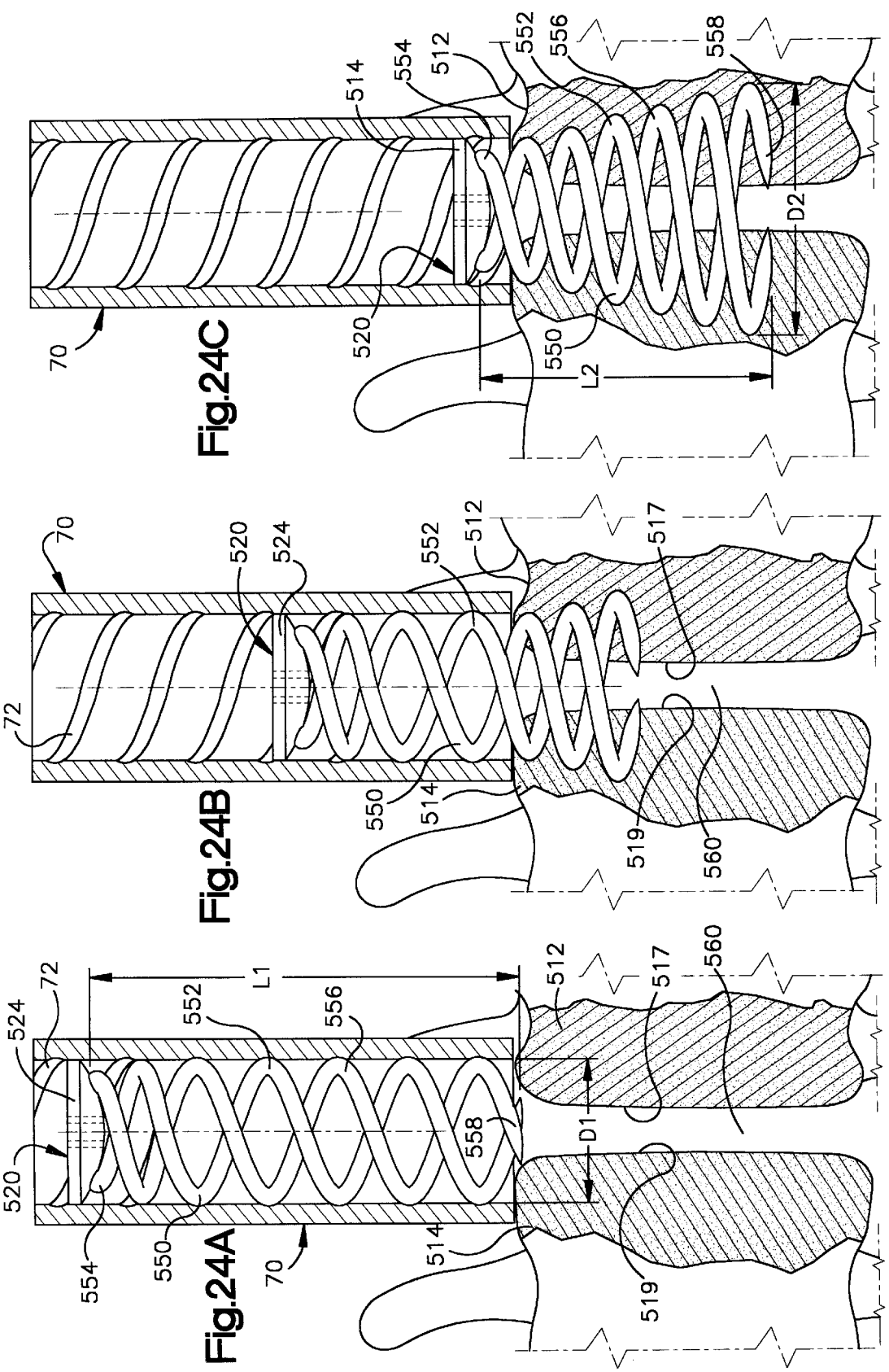

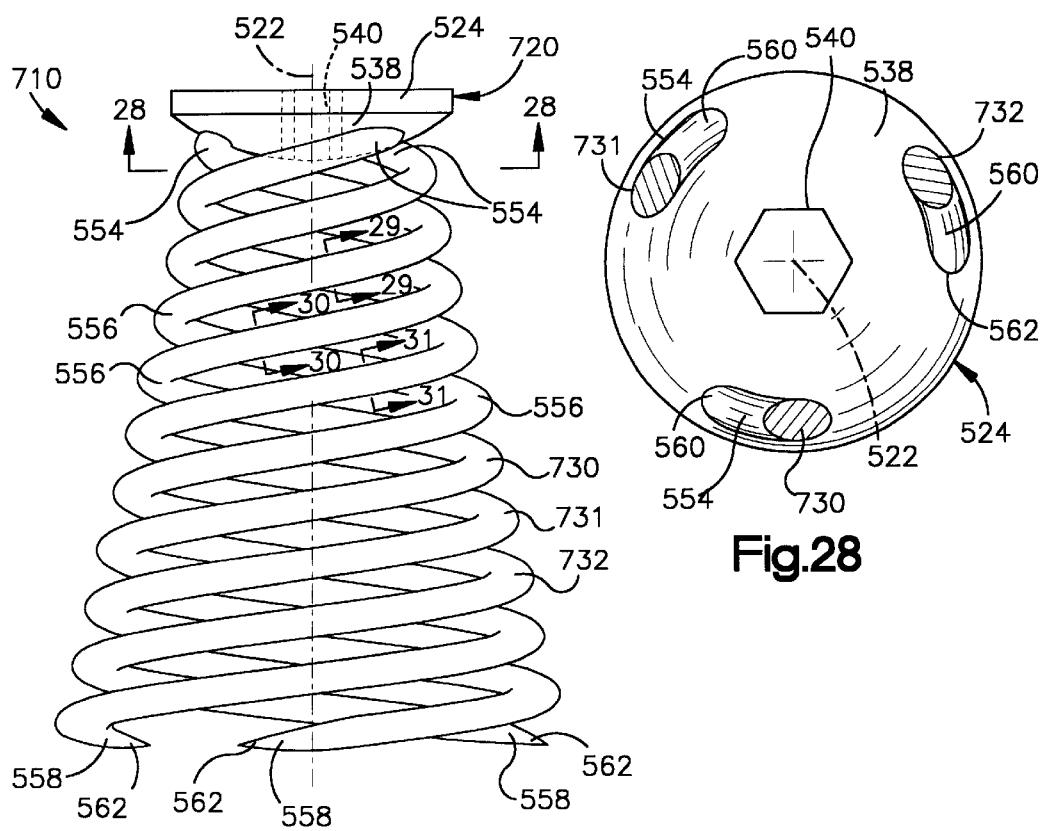
Fig.27
Fig.28
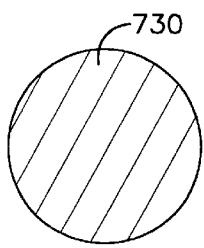
Fig.29
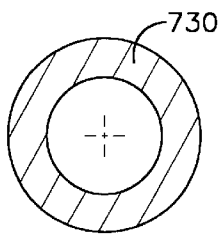
Fig.29A
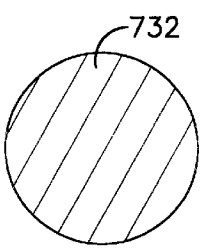
Fig.31
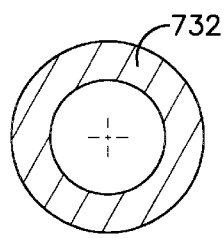
Fig.31A
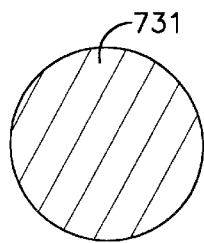
Fig.30
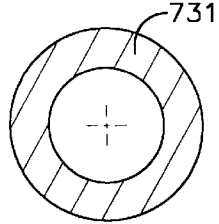
Fig.30A

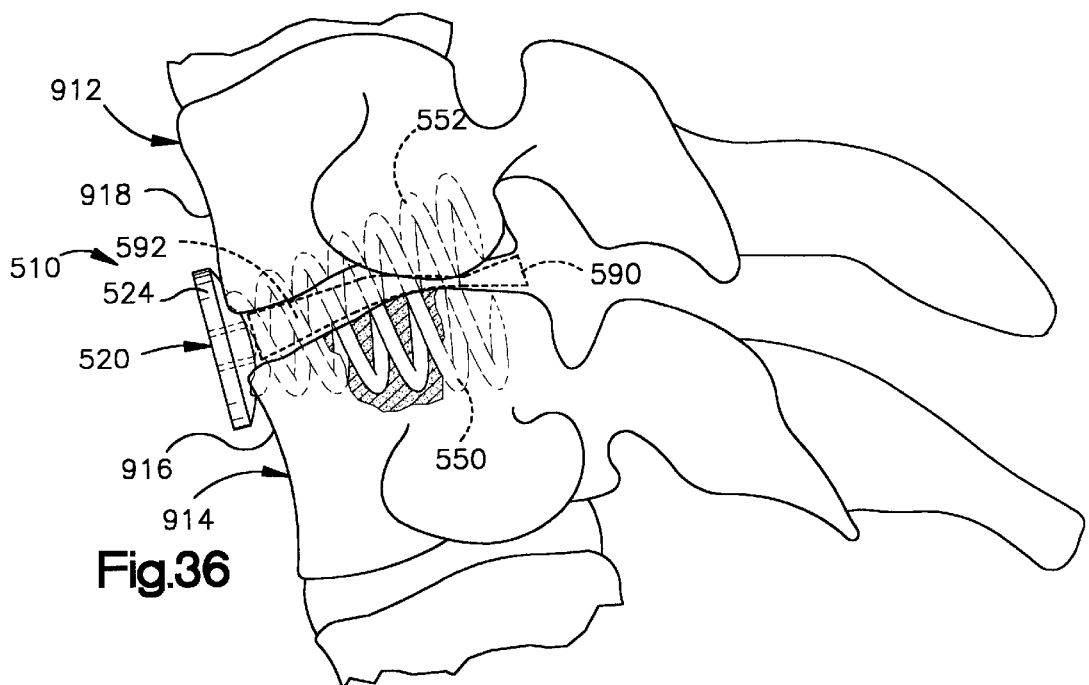
Fig.36
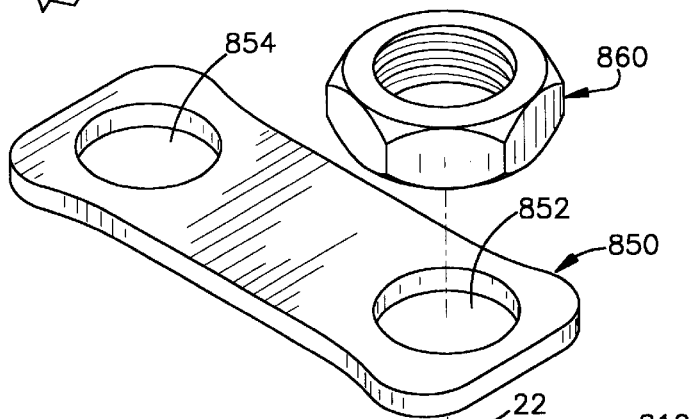
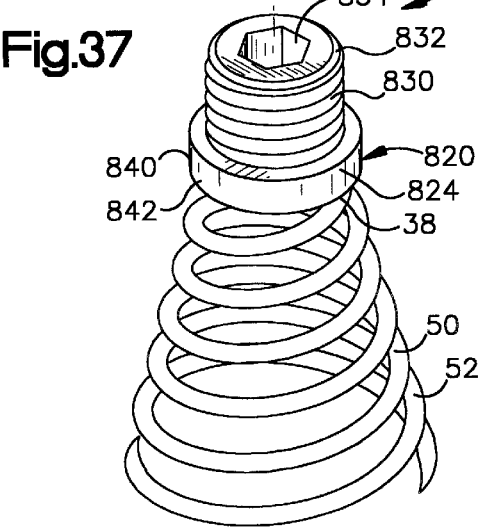
Fig.37

APPARATUS FOR IMPLANTATION INTO BONE

RELATED APPLICATIONS

This application is a continuation-in-part of co-pending U.S. patent application Ser. No. 09/781,847, entitled "APPARATUS FOR IMPLANTATION INTO BONE", filed Feb. 14, 2001, which is itself a continuation-in-part of co-pending U.S. patent application Ser. No. 09/708,940 filed Nov. 8, 2000 and Ser. No. 09/708,292, filed Nov. 8, 2000, now U.S. Pat. No. 6,469,309. The entire subject matter of the aformentioned three co-pending applications is in corporated herein by reference.

TECHNICAL FIELD

The present invention is directed to an apparatus for implantation into a bone in a patient's spine or pelvis, and is particularly directed to an apparatus that, when implanted, is resistant to toggling in the bone and to being pulled from the bone. The present invention is also directed to an apparatus for attaching and stabilizing adjacent vertebral bodies while the vertebral bodies fuse together.

BACKGROUND OF THE INVENTION

Bone screws are used in the medical field for a variety of purposes. Typical uses for bone screws, also referred as bone anchors, include treating a bone fracture, attaching a corrective device to parts of a fractured bone in an area adjacent to the fracture, and attaching a corrective device to a group of bones, such as vertebrae of a spinal column.

Most known bone screws use a conventional screw design, i.e. a solid shank, with one or more external thread convolutions. The solid shank and external threads of the conventional bone screws can cause the bone screws to displace an undesirably large amount of bone when implanted. Such conventional bone screws typically require a large amount of torque to implant the screw into a vertebral body. Furthermore, the resistance of the conventional screw to being pulled axially from the bone is dependent upon the surface area of the bone that interfaces with the screw threads.

It is also known to use a corkscrew-style helical spike as a tissue anchor. The known corkscrew-style tissue anchors, when implanted, displace less bone than the conventional bone screws, but are generally not able to withstand high tensile loads without structural failure. European Patent No. 0 374 088 A1 discloses a bone screw having a twin-corkscrew design.

One of the more challenging applications of a bone screw is implantation of the screw into the cancellous bone of a patient's spine or pelvis. For example, bone screws are frequently implanted into the cancellous bone of a patient's lumbar vertebrae during a spinal fixation procedure to correct scoliosis. Once implanted, the bone screws are used to mount suitable spinal fixation instrumentation, such as clamps, rods, and plates. Unfortunately, many of the known bonescrews, such as those described above, can be susceptible to toggling in the vertebral body and can also pull out of the vertebral body due to the substantial forces on the screws from human body movement and muscle memory. In order to achieve a high pull-out resistance, it is common to use additional screws, which results in an undesirably large amount of bone being displaced. In order to achieve a high pullout resistance, it is also known to thread a bone screw all of the way through a vertebrae and place a nut on the opposite side. However, use of such a nut increases the complexity of the surgical procedure.

Hence, it is desirable to provide an apparatus for implantation into a bone in a patient's spine or pelvis in a minimally invasive endoscopic procedure with a reduced amount of insertion torque required. The desirable apparatus would provide a platform for connecting spinal fixation instrumentation and, when implanted, be highly resistant to toggling in the bone and to being pulled out of the bone despite the substantial forces on the apparatus from human body movement and muscle memory.

Another application for an anchor or fastening-type apparatus in the field of spine surgery is the stabilization of adjacent vertebrae. Each adjacent pair of vertebrae in the human spinal column are separated by an intervertebral disc that makes relative movement of the vertebrae possible. Problems, however, can develop with one or more of the discs, causing severe back pain. In some cases, it is necessary to remove a problematic disc and to fuse the adjacent vertebrae together in order to relieve pain.

One known method for fusing an adjacent pair of vertebrae following removal of a disc is to implant a device, commonly referred to as a fusion cage, into the interbody space where the disc was removed. The fusion cage facilitates fusion of the vertebrae. Typically, procedures such as reaming and/or tapping of adjacent vertebrae are required to prepare the adjacent vertebrae to receive the fusion cage. Such procedures normally involve substantial cutting of the hard cortical bone of the end plates of the adjacent vertebrae, which can weaken the end plates and lead to collapse of the vertebrae. The fusion cage is then positioned in the interbody space and into engagement with the adjacent vertebrae. At least one known fusion cage has relatively movable parts that enable the fusion cage to be expanded after the fusion cage is positioned in the interbody space between adjacent vertebrae. The design of this expandable fusion cage is, however, relatively complex.

Typically, a fusion cage includes an internal cavity that is filled with bone graft material. The fusion cage and the bone graft material promote bone growth that slowly unites the adjacent vertebrae. The typical fusion cage, while in engagement with the adjacent vertebrae, does not attach to the vertebrae and thus does not resist relative movement of the vertebrae, through bending or rotation, along any one of the three planes of motion (sagittal, coronal, or horizontal). Rather, the typical fusion cage relies on the viscoelasticity of the surrounding ligaments to stabilize the adjacent vertebrae.

It is desirable to provide an apparatus for implantation into an adjacent pair of vertebral bodies that attaches to and thus fastens the vertebral bodies while they fuse together despite the forces on the apparatus from human body movement and muscle memory. It is further desirable to provide an apparatus which has a reduced insertion torque requirement, a simple one-piece construction, and which may be implanted into an adjacent pair of vertebrae without having to prepare the adjacent vertebrae to accept the apparatus by substantial cutting of the cortical bone.

SUMMARY OF THE INVENTION

The present invention is an apparatus for implantation into a bone in a patient's spine or pelvis. The apparatus, when implanted, is resistant to toggling in the bone and to being pulled from the bone. The apparatus comprises a platform for engaging a bone in a patient's spine or pelvis. The platform includes structure for connection to a spinal fixation implant. The apparatus further comprises at least one helical spike for embedding into the bone upon rotation of the platform. The at least one helical spike projects tangentially from the platform and extends around a longitudinal axis. The at least one helical spike has a tip portion at a distal end which penetrates into the bone as the platform is rotated. The at least one helical spike, when implanted, has a conical shape that increases in diameter as the at least one helical spike extends away from the platform.

In accordance with one feature of the present invention, the at least one helical spike has a first condition in which the at least one helical spike has a first maximum diameter and a second condition in which at least a portion of the at least one helical spike expands to a second maximum diameter that is larger than the first maximum diameter.

In accordance with another feature of the present invention, the at least one helical spike has a first axial length in the first condition and a second axial length in the second condition, the second axial length being smaller than the first axial length.

In accordance with yet another feature of the present invention, at least a portion of the at least one helical spike is made of a shape memory alloy that is responsive to changes in temperature above and below a predetermined temperature transition range, the at least one helical spike being in the first condition when the temperature of the at least one helical spike is below the predetermined temperature transition range, the at least one helical spike being in the second condition when heated above the predetermined temperature transition range, the at least one helical spike being implanted into the bone in the second condition.

In accordance with another embodiment, the present invention is an apparatus comprising at least one anchor for implantation into a bone. The anchor, when implanted, is resistant to toggling in the bone and to being pulled from the bone. The apparatus further comprises a spinal fixation implant for extending between and connecting a plurality of bones. The anchor includes a platform having a first surface for facing the bone. The platform further has structure for connection with the spinal fixation implant. The anchor further includes at least two helical spikes for embedding into the bone upon rotation of the platform. The at least two helical spikes are spaced apart and project tangentially from the first surface on the platform. The at least two helical spikes extend around a longitudinal axis. Each of the at least two helical spikes has a tip portion at a distal end which penetrates into the bone as the platform is rotated. The at least two helical spikes, when implanted, have a conical shape that increases as the at least two helical spikes extend away from the platform.

In accordance with yet another embodiment, the present invention is an apparatus for implanting an anchor into a bone in a patient's spine or pelvis. The apparatus comprises an anchor having a platform and at least one helical spike for embedding into the bone upon rotation of the platform. The platform faces a bone in a patient's spine or pelvis and includes structure for connection to a spinal fixation implant. The at least one helical spike projects tangentially from the platform and extends around a longitudinal axis. The at least one helical spike has a tip portion at a distal end which penetrates into the bone as the platform is rotated. The at least one helical spike has a first condition in which the at least one helical spike has a first maximum diameter and a second condition in which at least a portion of the at least one helical spike expands to a second maximum diameter that is larger than the first maximum diameter. The anchor, when implanted, is resistant to toggling in the bone and to being pulled from the bone.

In accordance with a feature of the present invention, the apparatus further comprises a tubular sleeve for receiving the anchor. The tubular sleeve has an inside diameter that is approximately equal to the first maximum diameter of the at least one helical spike of the anchor. The anchor is positionable inside the tubular sleeve when in the first condition.

In accordance with still another embodiment, the present invention comprises an apparatus for implantation into an adjacent pair of vertebral bodies having first and second surfaces that oppose each other. The apparatus, when implanted, is attached to the adjacent pair of vertebral bodies and stabilizes the vertebral bodies while the vertebral bodies fuse together. The apparatus comprises a platform having a third surface extending transverse to the first and second surfaces. The apparatus further comprises at least one helical spike for embedding into each of the adjacent pair of vertebral bodies upon rotation of the platform to attach the at least one helical spike to each of the vertebral bodies and thus fasten (pin) the vertebral bodies together. The at least one helical spike projects from the platform and extends around a longitudinal axis. The at least one helical spike has a tip portion at a distal end for penetrating the first and second surfaces and for screwing into the adjacent pair of vertebral bodies as the platform is rotated. The at least one helical spike at least partially defines an internal cavity for receiving material that promotes fusion of the vertebral bodies. The at least one helical spike, when implanted, has a conical shape that increases in diameter as the at least one helical spike extends away from the platform.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 7A is a side view, partially in section, illustrating the apparatus of FIG. 3 in a first condition prior to implantation in the vertebral body;

FIG. 7B is a view similar to FIG. 7A illustrating the apparatus of FIG. 3 during implantation in the vertebral body;

FIG. 7C is a view similar to FIG. 7A illustrating the apparatus of FIG. 3 in a second condition following implantation in the vertebral body;

FIG. 14 is a schematic view, partially in section, of a third embodiment of the present invention;

FIG. 15 is an exploded perspective view of the apparatus of FIG. 14;

FIG. 16 is a sectional view taken along line 16—16 in FIG. 14;

FIG. 16A is a sectional view similar to FIG. 16 illustrating an alternate configuration;

FIG. 17 is a sectional view taken along line 17—17 in FIG. 14;

FIG. 17A is a sectional view similar to FIG. 17 illustrating an alternate configuration;

FIG. 20 is a side view of the apparatus of FIG. 18;

FIG. 21 is a sectional view taken along 21—21 in FIG. 20;

FIG. 21A is a sectional view similar to FIG. 21 illustrating an alternate configuration;

FIG. 22 is a sectional view taken along 22—22 in FIG. 20;

FIG. 22A is a sectional view similar to FIG. 22 illustrating an alternate configuration;

FIG. 24A is a side view, partially in section, illustrating the apparatus of FIG. 20 in a first condition prior to implantation into the adjacent pair of vertebral bodies;

FIG. 24B is a view similar to FIG. 24A illustrating the apparatus of FIG. 20 during implantation the adjacent pair of vertebral bodies FIG. 24C is a view similar to FIG. 24A illustrating the apparatus of FIG. 20 in a second condition following implantation the adjacent pair of vertebral bodies;

FIG. 27 is a side view illustrating an apparatus for implanting in an adjacent pair of vertebral bodies in accordance with a sixth embodiment of the present invention;

FIG. 28 is a sectional view taken along line 28—28 in FIG. 27;

FIG. 29 is a sectional view taken along 29—29 in FIG. 27;

FIG. 29A is a sectional view similar to FIG. 29 illustrating an alternate configuration;

FIG. 30 is a sectional view taken along 30—30 in FIG. 27;

FIG. 30A is a sectional view similar to FIG. 30 illustrating an alternate configuration;

FIG. 31 is a sectional view taken along 31—31 in FIG. 27;

FIG. 31A is a sectional view similar to FIG. 31 illustrating an alternate configuration;

FIG. 36 is a side view illustrating a cervical application of the apparatus of FIG. 20 in accordance with the present invention;

FIG. 37 is an exploded perspective view illustrating an apparatus constructed in accordance with a seventh embodiment of the present invention;

DESCRIPTION OF PREFERRED EMBODIMENTS

The present invention is directed to an apparatus for implantation into a bone in a patient's spine or pelvis, and is particularly directed to an apparatus that, when implanted, is resistant to toggling in the bone and to being pulled from the bone. The present invention is also directed to an apparatus for attaching and stabilizing adjacent vertebral bodies while the vertebral bodies fuse together.

Figure 1:
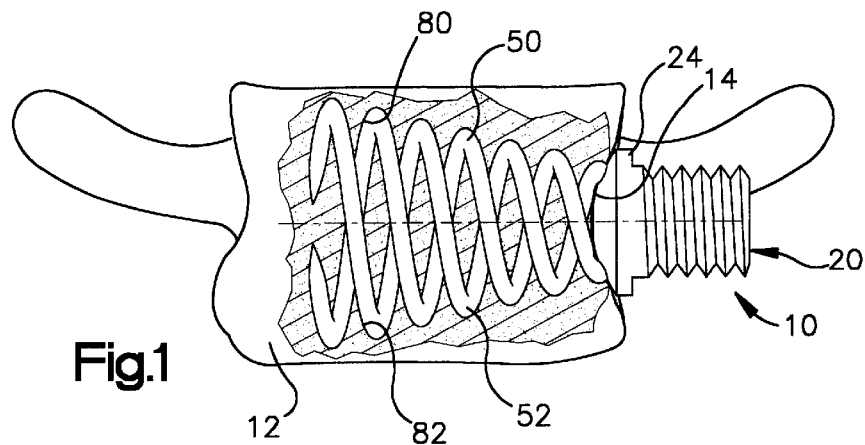
FIG. 1 is a schematic anterior view of an apparatus constructed in accordance with the present invention implanted in a vertebral body.

As representative of the present invention, FIG. 1 illustrates an apparatus 10 implanted in a lumbar vertebrae 12. It should be understood that the apparatus 10 could be implanted into any vertebral body, including the sacrum. The lumbar vertebrae 12 has a concave side surface 14.

The apparatus 10 comprises an anchor 20 made from a biocompatible material. Known biocompatible materials include titanium, stainless steel, and spring steel. It is contemplated that the biocompatible material used for the anchor 20 could be polymeric or composite in nature. In accordance with one feature of the present invention, the anchor 20 is at least partially made from a shape memory alloy that is biocompatible. As is known in the art, shape memory alloys have the ability to return to a predetermined shape when heated. When a shape memory alloy is cold, or below its transition temperature range (TTR), the material has a low yield strength and can be deformed into a new shape, which it will retain until heated. However, when a shape memory alloy is heated above its TTR, the material undergoes a change in crystal structure (from a martensite structure to an austensite structure), which causes the material to return to its original, or "memorized" shape. A memorized shape is imprinted into a shape memory alloy by first holding the material in the desired shape at a high temperature, and then continuing to hold the material in the desired shape as it cools through its TTR.

Figure 3:
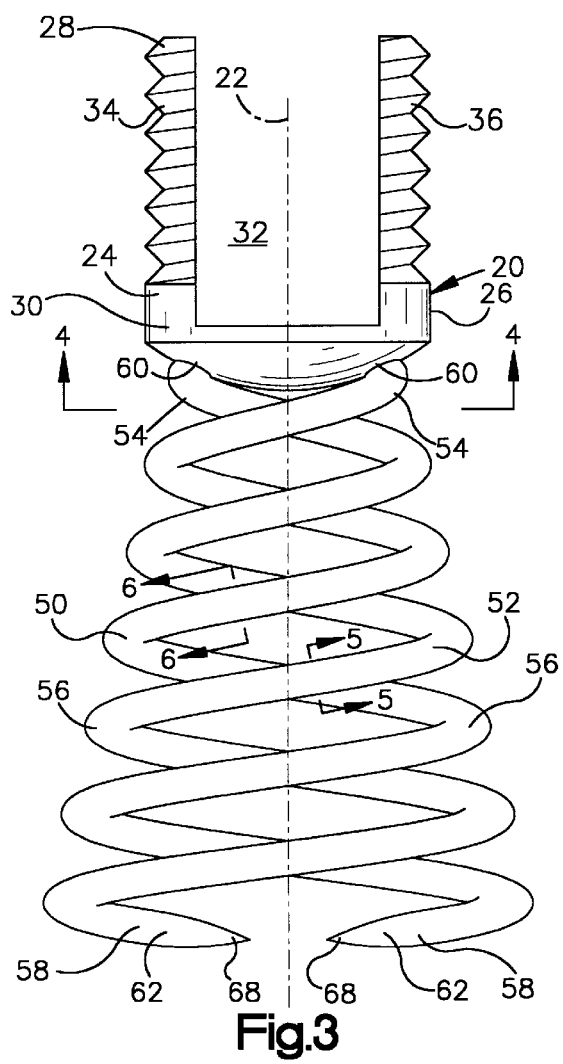
FIG. 3 is a side view of the apparatus of FIG. 1.

As shown in FIG. 3, the anchor 20 is centered about a longitudinal axis 22. The anchor 20 includes a platform 24 having a generally cylindrical outer surface 26 extending between oppositely disposed first and second ends 28 and 30 of the platform. The platform 24 includes a generally rectangular slot 32 that extends axially from the first end 28 toward the second end 30 of the platform. Adjacent the first end 28, the outer surface 26 of the platform 24 includes oppositely disposed segments of external threads 34 and 36 that are separated by the slot 32. The slot 32 and the threads 34 and 36 provide structure for connecting spinal fixation instrumentation to the platform 24 as discussed further below.

The second end 30 of the platform 24 includes an end surface 38 having a convex shape that is complimentary to the shape of the concave side surface 14 of the vertebrae 12. It should be understood that the end surface 38 of the platform 24 could be any shape necessary to remain complimentary to the shape of the side surface 14 of the vertebrae 12. The end surface 38 of the platform 24 may include barbs (not shown) or other suitable structure for fixedly engaging the side surface 14 of the vertebrae 12. Further the end surface 38 of the platform 24 may also be porous, pitted, or have a biocompatible surface coating to assist with fixation of the anchor 20 to the vertebrae 12.

Figure 5:
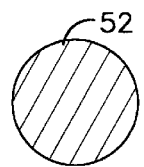
FIG. 5 is a sectional view taken along 5—5 in FIG. 3.
Figure 5A:
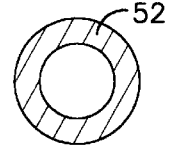
FIG. 5A is a sectional view similar to FIG. 5 illustrating an alternate configuration.
Figure 6:
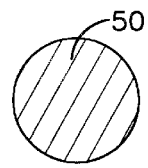
FIG. 6 is a sectional view taken along 6—6 in FIG. 3.
Figure 6A:
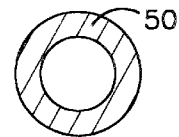
FIG. 6A is a sectional view similar to FIG. 6 illustrating an alternate configuration.

First and second helical spikes 50 and 52 project tangentially from the end surface 38 of the platform 24. The helical spikes 50 and 52 resemble a pair of intertwined corkscrews, both of which have a conical shape that increases in diameter as the helical spikes extend away from the platform 24. As shown in FIGS. 5 and 6, each of the helical spikes 50 and 52 has a solid cross-section. Alternatively, each of the helical spikes 50 and 52 could have a tubular cross-section, as illustrated in FIGS. 5A and 6A, which provides a means for matching the modulus of elasticity of the bone.

According to the embodiment illustrated in FIGS. 1–7, the first and second helical spikes 50 and 52 extend around the axis 22. The helical spikes 50 and 52 extend symmetrically in a conical pattern about the axis 22. It is contemplated, however, that the conical shape of the first and second helical spikes 50 and 52 could be different from each other (i.e., one spike being a smaller cone than the other spike).

In the illustrated embodiment of FIGS. 1–7, the first and second helical spikes 50 and 52 have the same axial length, and also have the same cross-sectional shape. It is contemplated, however, that the first and second helical spikes 50 and 52 could have different axial lengths. Further, it is contemplated that the helical spikes 50 and 52 could have a different cross-sectional shape, such as an oval shape. It also contemplated that the first and second helical spikes 50 and 52 could have different diameters (i.e., one spike being thicker than the other spike). Finally, it is contemplated that the helical spikes 50 and 52 should have the same pitch, and that the pitch of the helical spikes would be selected based on the specific surgical application and quality of the bone in which the anchor 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the end surface 38 of the platform 24. The connecting portion 54 may include barbs (not shown) for resisting pull-out of the helical spikes 50 and 52 from the vertebrae 12. According to one method for manufacturing the anchor 20, the connecting portion 54 of each of the helical spikes 50 and 52 is fixedly attached to the platform 24 by inserting, in a tangential direction, the proximal ends 60 of the helical spikes into openings (not shown) in the end surface 38 and welding the connecting portions 54 to the platform. The inserted proximal ends 60 of the helical spikes 50 and 52 help to reduce bending stresses on the helical spikes under tensile or shear loads.

Figure 4:
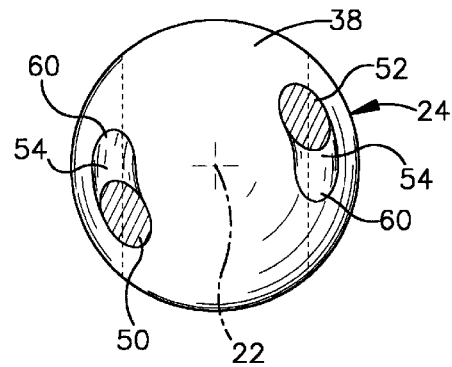
FIG. 4 is a sectional view taken along 4—4 in FIG. 3.

Alternatively, the helical spikes 50 and 52 may be formed integrally with the platform 24, such as by casting the anchor 20. If the anchor 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connection portions 54 of the helical spikes under tensile or shear loads. As best seen in FIG. 4, the connecting portions 54 at the proximal ends 60 of the first and second helical spikes 50 and 52 are spaced 180° apart about the axis 22 to balance the anchor 20 and evenly distribute loads on the helical spikes.

The tip portion 58 of each of the helical spikes 50 and 52 is located at a distal end 62 of the helical spikes. The intermediate portion 56 of each of the helical spikes 50 and 52 extends between the tip portion 58 and the connecting portion 54. The intermediate portion 56 and the tip portion 58 of each of the helical spikes 50 and 52 have a diameter that is less than or equal to the diameter of the connecting portions 54. If the diameter of the intermediate portion 56 and the tip portion 58 is less than the diameter of the connecting portion 54 of each of the helical spikes 50 and 52, the increased thickness of the connecting portions will help to provide the anchor 20 with increased tensile strength at the junction of the helical spikes and the platform 24.

Figure 32:
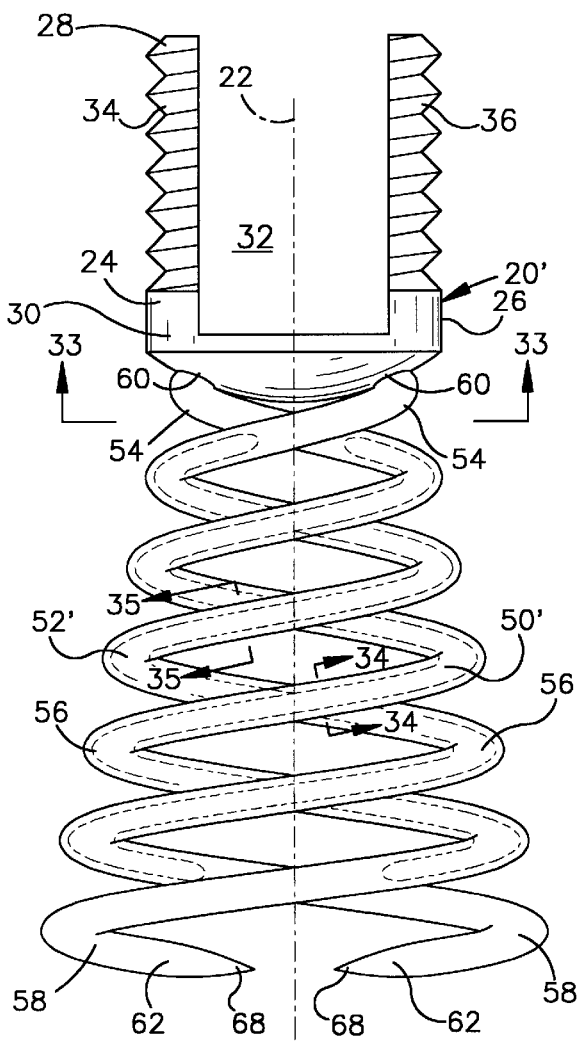
FIG. 32 is a side view, similar to FIG. 3, illustrating a modification of the present invention.
Figure 33:
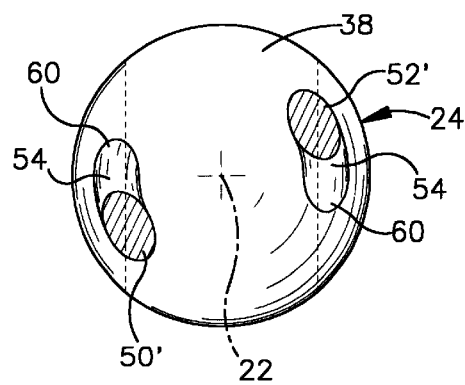
FIG. 33 is a sectional view taken along line 33—33 in FIG. 32.
Figure 34:
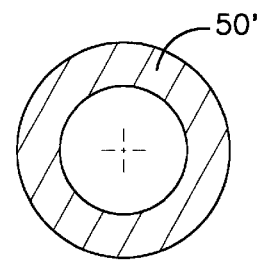
FIG. 34 is a sectional view taken along line 34—34 in FIG. 32.
Figure 35:
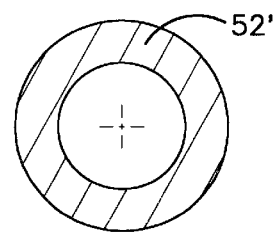
FIG. 35 is a sectional view taken along line 35—35 in FIG. 32.

FIGS. 32–35 illustrate modified configuration for the anchor 20 in accordance with the present invention. As shown in FIG. 32, an anchor 20' has helical spikes 50' and 52'. FIGS. 32–35 illustrate that the connecting portions 54 and/or the tip portions 58 of the helical spikes 50' and 52' could have a solid cross-section, while the intermediate portions 56 have a tubular cross-section. Such modified configurations of the anchor 20' provide additional means for matching the modulus of elasticity of the bone. The aforementioned variations in the configuration of the anchors 20 and 20' allow the surgeon to select a particular configuration based on the specific surgical application and quality of the bone in which the anchor is to be implanted.

Figure 8:
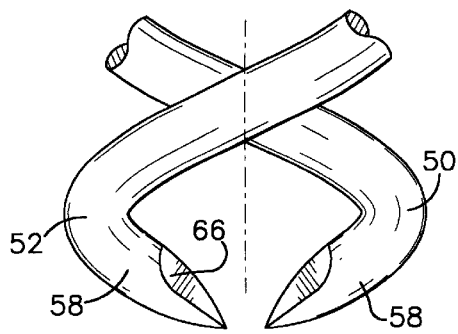
FIG. 8 illustrates an alternate configuration for an end portion of the apparatus of FIG. 1.

Returning now to FIGS. 1–7, the tip portion 58 of each of the helical spikes 50 and 52 has an elongated conical shape with a sharp pointed tip 68 for penetrating into the vertebrae 12 as the platform 24 of the anchor 20 is rotated in a clockwise direction. FIG. 8 illustrates an alternative, self-tapping configuration for the tip portions 58 which includes a planar surface 66 for driving into the vertebrae 12, in the same manner that a wood chisel turned upside-down drives into wood, as the platform 24 is rotated. It is contemplated that the tip portions 58 could also have a pyramid shape (not shown), similar to the tip of a nail. Although the outer surfaces of the helical spikes 50 and 52 are shown as being relatively smooth in FIGS. 1–7, it is contemplated that the outer surfaces may instead be porous, pitted, or have a biocompatible coating to assist with fixation of the anchor 20 to the vertebrae 12.

As mentioned previously, the anchor 20 is made from a shape memory alloy, which allows the anchor to have more than one shape. FIGS. 7A–7C illustrate the shapes of the anchor 20 at various stages of the implantation process. The shape that is "memorized" into the material of the anchor 20 is illustrated in FIGS. 1–3 and 7C. FIG. 7A illustrates the anchor 20 in a first condition prior to implantation in the vertebrae 12. In the first condition, the helical spikes 50 and 52 of the anchor 20 do not have a conical shape, but instead have a generally cylindrical shape with a uniform maximum diameter D1. Further, in the first condition, the helical spikes 50 and 52 have an axial length L1. In order for the anchor 20 to take the shape of the first condition, the temperature of the anchor must be below its TTR so that the material of the anchor is soft and ductile.

The anchor 20 is moved into the first condition of FIG. 7A with the aid of a tubular sleeve 70. The sleeve 70 is made from a hard metal and includes internal threads 72 (FIG. 7B) for mating with the helical spikes 50 and 52 of the anchor 20 to aid in drawing the helical spikes into the sleeve upon rotation of the anchor. With the temperature of the anchor 20 below its TTR, the anchor is pulled into the sleeve 70 by rotating the platform 24 in a first direction with a driver (not shown) that fits into the slot 32. As the helical spikes 50 and 52 are drawn into the sleeve 70, the helical spikes are compressed radially inward, causing their axial length to grow to the axial length L1.

FIG. 7B illustrates the anchor 20 during implantation into the vertebrae 12. As shown in FIG. 7B, the helical spikes 50 and 52 emerge from the sleeve 70 when the platform 24 is rotated in a second direction that is opposite the first direction. As the helical spikes 50 and 52 emerge from the sleeve 70, it is desired that the helical spikes return to the memorized conical shape of FIG. 3. To return the helical spikes 50 and 52 to the conical shape as they emerge from the sleeve 70, heat is applied to the anchor 20 until the temperature of the anchor exceeds the TTR for the shape memory material. Simple body temperature may be sufficient to raise the temperature of the anchor 20 above its TTR. If additional heat is needed, heat may be applied in many ways, such as passing electric current through a wire connected with the anchor 20 or the sleeve 70, transmitting radio waves that inductively heat the anchor, or applying a hot saline pack to the sleeve.

With the helical spikes 50 and 52 expanding radially, but contracting axially, as they emerge from the sleeve 70, the helical spikes are implanted in the vertebrae 12 in the conical shape, or second condition, illustrated in FIG. 7C. As shown in FIG. 7C, in the implanted second condition, the helical spikes 50 and 52 have a maximum diameter D2 that is larger than the maximum diameter D1 of the helical spikes in the first condition. Further, in the implanted second condition, the helical spikes 50 and 52 have an axial length L2 that is smaller than the axial length of the helical spikes in the first condition.

It is contemplated that the first and second conditions of the helical spikes 50 and 52 described above could be achieved even if only certain portions of the helical spikes were made from a shape memory alloy. For example, it is contemplated that the tip portions 58 and the intermediate portions 56 of the helical spikes 50 and 52 could be made from a shape memory alloy, while the connecting portions 54 are made from another biocompatible metal. Further, it should be understood that if a shape memory material is not used at all in the helical spikes 50 and 52 and a material such as spring steel is used instead, the helical spikes would still be able to be compressed in to the first condition of FIG. 7A, and expand into the second condition upon implantation as shown in FIGS. 7B and 7C.

Turning now to a more detailed discussion of the procedure for implanting the anchor 20, a tool (not shown) is used to punch two holes (not shown) in the cortical bone (not shown) of the vertebrae 12. The holes are punched in locations that correspond to the spacing of the tip portions 58 of the helical spikes 50 and 52 on the anchor 20 in the first condition of FIG. 7A. It should be noted that one or both of the configurations of the tip portions 58 illustrated in FIGS. 1–8 may be able to punch through the cortical bone upon rotation of the anchor 20, thus eliminating the need for the aforementioned tool to punch holes in the cortical bone. The tip portions 58 are then placed in the holes in the vertebrae 12 and a rotatable driver (not shown) is inserted into the slot 32 in the platform 24. The helical spikes 50 and 52 are then heated, as discussed above, to a temperature above the TTR for the shape memory material. The driver is then rotated, causing the anchor 20 to rotate as well.

Rotation of the anchor 20 screws the helical spikes 50 and 52 into the cancellous bone of the vertebrae 12. The tangentially-oriented connection between the connecting portions 54 of the helical spikes 50 and 52 and the platform 24, as well as the constraining function of the sleeve 70, minimizes bending loads on the connecting portions during rotation of the anchor 20. Further, the tangentially-oriented connection ensures that the force vector resulting from torque and axial force applied by the driver to the platform 24 is transmitted along the helical centerline (not shown) of each of the helical spikes 50 and 52.

As the anchor 20 is rotated, the tip portion 58 of the first helical spike 50 penetrates the cancellous bone and cuts a first helical tunnel 80 (FIG. 1) through the vertebrae 12. Simultaneously, the tip portion 58 of the second helical spike 52 penetrates the cancellous bone of the vertebrae 12 and cuts a second helical tunnel 82. Continued rotation of the anchor 20 embeds the helical spikes 50 and 52 deeper into the cancellous bone of the vertebrae 12. The first and second helical tunnels 80 and 82 are shaped like the conical configuration of the helical spikes 50 and 52, respectively, in the second condition. The anchor 20 is rotated until the convex end surface 38 of the platform 24 seats against the concave side surface 14 of the vertebrae 12 as shown in FIG. 1.

Because the helical spikes 50 and 52 of the anchor 20 displace much less of the cancellous bone of the vertebrae 12 during implantation than a conventional solid shank bone screw, much less torque is required to implant the anchor in the vertebrae than is required by a conventional bone screw. Further, because the helical spikes 50 and 52 displace only a small amount of bone, the helical spikes do not create a core defect that could lead to bone deformation or failure, such as the helical spikes pulling out of the vertebrae 12. Advantageously, the conical shape of the helical spikes 50 and 52 increases the amount of surface area engaged by the anchor 20, spreads any load on the anchor out over different areas of the vertebrae 12, and provides fixation over a larger volume of bone. The aforementioned advantages of the conical shape of the helical spikes 50 and 52 is especially helpful when implanting the anchor 20 in osteoporotic bone.

Figure 2:
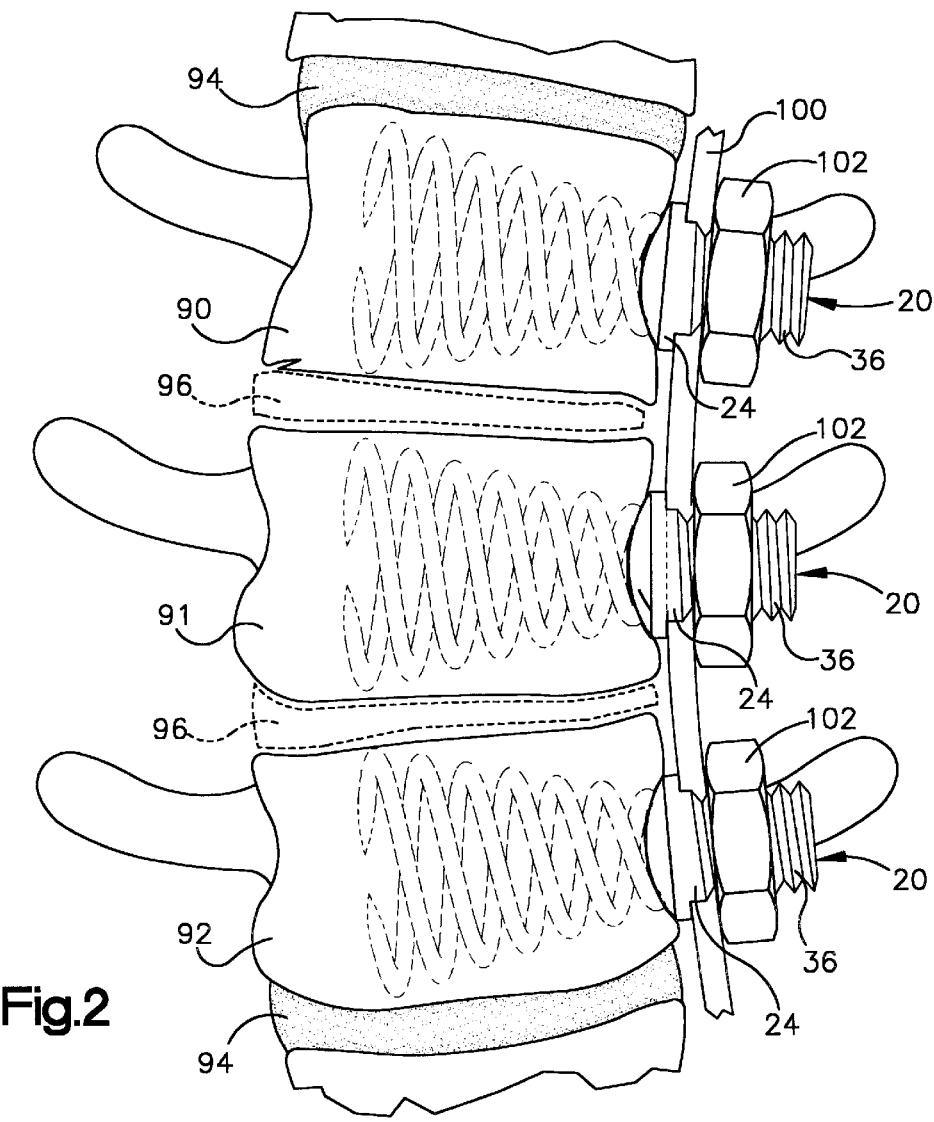
FIG. 2 is a schematic anterior view of several vertebral bodies implanted with the apparatus of FIG. 1 and connected by a spinal fixation implant in accordance with the present invention.

FIG. 2 illustrates how the anchor 20 is used for segmental spinal fixation of lumbar vertebrae to treat a patient with scoliosis. Lumbar vertebrae L2–L4, indicated by reference numbers 90, 91, and 92, respectively, are shown in FIG. 2. Normally, disk material 94 separates each of the lumbar vertebrae 90–92. However, in order to correct the scoliosis, the surgeon removes the disk material 94 between the vertebrae 90–92 . The spaces left between the vertebrae 90–92 are subsequently filled with bone graft material 96 (shown schematically in FIG. 2) that fuses the vertebrae together over time. Spinal fixation instrumentation, such as a rod or a beam 100, is used to achieve and maintain correction of the scoliosis and support the vertebrae 90–92 until the vertebrae fuse together.

As shown in FIG. 2, the vertebrae 90–92 are each implanted with the anchor 20 according to the present invention as described above. The beam 100, which is bent into a desired shape by the surgeon, is placed into the slot 32 in each of the anchors 20. A nut 102 is then screwed onto the threads 34 and 36 on each of the platforms 24 and is tightened to secure the beam 100 to each of the anchors 20.

When implanted, the anchors 20 are subjected to substantial forces caused by human body movement and muscle memory. In some cases, these forces can tend to pull the known screws used in such an application out of the vertebrae 90–92 or can cause the screws to toggle in the vertebrae. However, when the helical spikes 50 and 52 are embedded in the vertebrae 90–92, the conical shape of the two helical spikes of the anchors 20 provides the anchors with a high resistance to pull-out forces and a high resistance to toggling in the vertebrae 90–92. As mentioned previously, the conical shape of the helical spikes 50 and 52 increases the amount of surface area engaged by the anchor 20, distributes any load on the anchor, and provides fixation over a larger volume of bone. Finally, the use of a shape memory alloy for the helical spikes 50 and 52 allows the anchor 20 to have a smaller diameter prior to implantation, which permits minimally invasive endoscopic surgery through a cannula, and a wider diameter when implanted, which improves fixation in the vertebrae.

FIGS. 9–13 illustrate an apparatus 210 constructed in accordance with a second embodiment of the present invention. In the second embodiment of FIGS. 9–13, reference numbers that are the same as those used in the first embodiment of FIGS. 1–7 designate parts that are the same as parts in the first embodiment.

Figure 11:
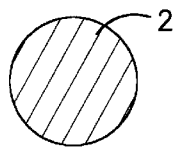
FIG. 11 is a sectional view taken along 11—11 in FIG. 9.
Figure 11A:
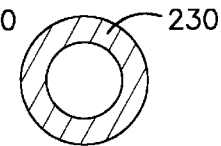
Figure 12:
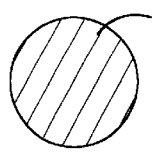
FIG. 12 is a sectional view taken along 12—12 in FIG. 9.
Figure 12A:
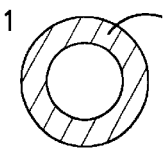
Figure 13:
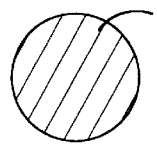
FIG. 13 is a sectional view taken along 13—13 in FIG. 9.
Figure 13A:
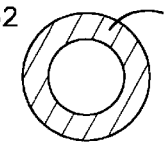

According to the second embodiment, the apparatus 210 comprises an anchor 220 having three helical spikes 230, 231, and 232 projecting tangentially from the end surface 38 of the platform 24. The spikes 230–232 extend around the axis 22 and have a conical shape that increases in diameter as the helical spikes extend away from the platform. As shown in FIGS. 11–13, each of the helical spikes 230–232 has a solid cross-section. Alternatively, each of the helical spikes 230–232 could have a tubular cross-section as shown in FIGS. 11A–13A, which provides a means for matching the modulus of elasticity of the bone.

Figure 9:
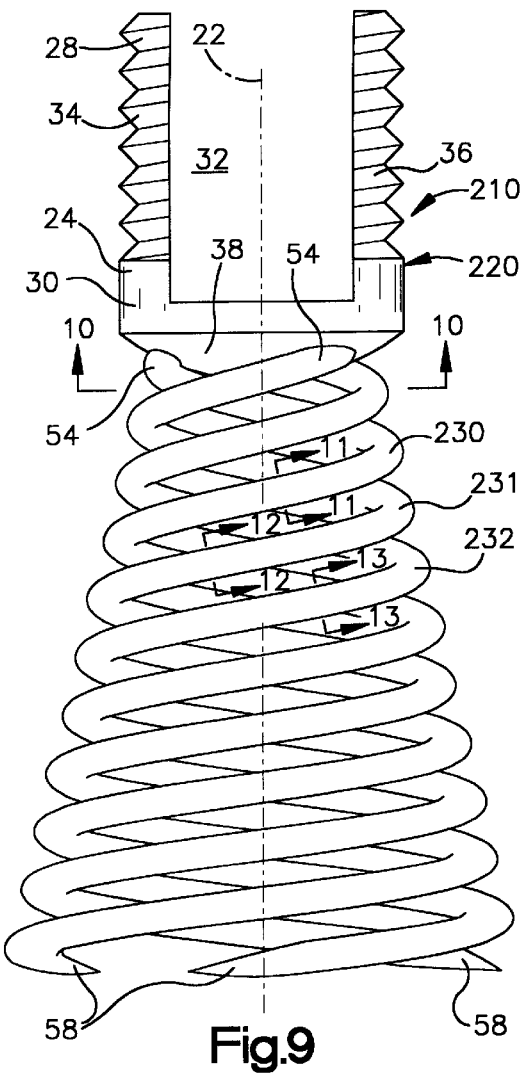
FIG. 9 is a side view illustrating a second embodiment of an apparatus in accordance with the present invention.
Figure 10:
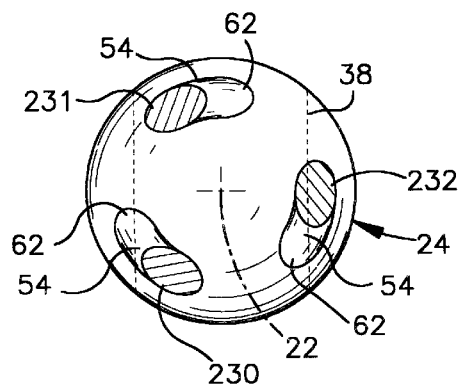
FIG. 10 is a sectional view taken along line 10—10 in FIG. 9.

As shown in FIG. 10, the connecting portions 54 at the proximal ends 60 of the helical spikes 230–232 are spaced 120° apart about the axis 22, which balances the anchor 220 and evenly distributes loads on the helical spikes. As in the first embodiment of FIGS. 1–7, in the second embodiment of FIGS. 9–13, the outer diameter of the connecting portions 54 of the helical spikes 230–232 is greater than or equal to the outer diameter of the intermediate portions 56 and the tip portions 58 of the helical spikes.

The three helical spikes 230–232 extend symmetrically in a conical pattern about the axis 22. It is contemplated, however, that the conical shape of one or more of the helical spikes 230–232 could be different from the other(s) (i.e., one spike being a smaller cone than the others). As shown in FIG. 9, the three helical spikes 230–232 have the same axial length and also have the same cross-sectional shape. It is contemplated, however, that one or more of the helical spikes 230–232 could have different axial lengths. Further, it is contemplated that one or more of the helical spikes 230–232 could have a different cross-sectional shape, such as an oval shape. It also contemplated that the one or more of the helical spikes 230–232 could have different diameters (i.e., one spike being thicker or thinner than the other spike(s)). Finally, it is contemplated that the helical spikes 230–232 should have the same pitch, and that the pitch of the helical spikes would be selected based on the specific surgical application and quality of the bone in which the anchor 20 is to be implanted.

It is contemplated that the modified configurations of the helical spikes 50' and 52' illustrated in FIGS. 32–35 could also be applied to the second embodiment of FIGS. 9–13. Specifically, the connecting portions 54 and/or the tip portions 58 of the helical spikes 230–232 could have a solid cross-section, while the intermediate portions 56 have a tubular cross-section. Such modified configurations of the anchor 220 provide additional means for matching the modulus of elasticity of the bone.

The tip portion 58 of each of the helical spikes 230–232 illustrated in FIG. 9 has an elongated conical shape for penetrating into a vertebrae as the platform 24 of the anchor 220 is rotated in the clockwise direction. It should be understood that the tip portions 58 of the helical spikes 230–232 of the anchor 220 could alternatively be configured like the tip portions illustrated in FIG. 8. Further, although the outer surfaces of the helical spikes 230–232 are shown as being smooth in FIGS. 9–13, it is contemplated that the outer surfaces may instead be porous, pitted, or have a biocompatible coating to assist with fixation of the anchor 220 to the vertebrae.

The helical spikes 230–232 of the anchor 220 according to the second embodiment of FIGS. 9–13 are also made of a shape memory alloy and are implanted in a vertebrae in the same manner as the anchor 20 according to the first embodiment. The shapes of the anchor 220 at various stages of the implantation process are similar to that which is illustrated in FIGS. 7A–7C for the anchor 20 of the first embodiment. Hence, the shape that is "memorized" into the material of the anchor 220 is illustrated in FIG. 9. Further, the anchor 220 has a first condition (not shown) prior to implantation in a vertebrae in which the helical spikes 230–232 do not have a conical shape, but instead have a generally cylindrical shape with a first maximum diameter. In addition, in the first condition, the helical spikes 230–232 have a first axial length. In order for the anchor 220 to take the shape of the first condition, the temperature of the anchor must be below its TTR so that the material of the anchor is soft and ductile. As in the first embodiment of FIGS. 1–7, the anchor 220 is also moved into the first condition with the aid of the tubular sleeve 70.

To return the helical spikes 230–232 to the conical shape as they emerge from the sleeve 70, heat is applied to the anchor 220 until the temperature of the anchor exceeds the TTR for the shape memory material. With the helical spikes 230–232 expanding radially and contracting axially as they emerge from the sleeve 70, the helical spikes are implanted in a vertebrae in the conical shape, or second condition, as illustrated in FIG. 7C for the first embodiment. In the implanted second condition, the helical spikes 230–232 have a second maximum diameter that is larger than the first maximum diameter of the helical spikes in the first condition. Further, in the implanted second condition, the helical spikes 230–232 have a second axial length that is smaller than the first axial length of the helical spikes in the first condition.

It is contemplated that the first and second conditions of the helical spikes 230–232 described above could be achieved even if only certain portions of the helical spikes were made from a shape memory alloy. For example, it is contemplated that the tip portions 58 and the intermediate portions 56 of the helical spikes 230–232 could be made from a shape memory alloy, while the connecting portions 54 are made from another biocompatible metal. Further, if a shape memory material is not used at all in the helical spikes 230–232 and a material such as spring steel is used instead, the helical spikes would still be able to be compressed into the first condition and expand into the second condition upon implantation.

It should be understood that the anchor 220 according to the second embodiment is also designed to be used to mount spinal fixation instrumentation in the same manner as the anchor 20 according to the first embodiment.

Because the helical spikes 230–232 of the anchor 220 displace less cancellous bone during implantation than a conventional solid shank bone screw, less torque is required to implant the anchor in a vertebrae than is required by a conventional bone screw. Further, the conical shape of the helical spikes 230–232 according to the second embodiment, when implanted in a vertebrae, make the anchor 220 highly resistant to being pulled out of the vertebrae and to toggling in the vertebrae despite being subjected to substantial forces caused by human body movement and muscle memory. As mentioned previously, the conical shape of the helical spikes 230–232 increases the amount of surface area engaged by the anchor 220, distributes any load on the anchor, and provides fixation over a larger volume of bone. Finally, the use of a shape memory alloy for the helical spikes 230–232 allows the anchor 220 to have a smaller diameter prior to implantation, which permits minimally invasive endoscopic surgery through a cannula, and a wider diameter when implanted, which improves fixation in a vertebrae.

FIGS. 14–17 illustrate an apparatus 410 constructed in accordance with a third embodiment of the present invention. In the third embodiment of FIGS. 14–17, reference numbers that are the same as those used in the first embodiment of FIGS. 1–7 designate parts that are the same as parts in the first embodiment.

According to the third embodiment, the apparatus 410 comprises an identical pair of anchors 420 extending around a longitudinal axis 422. Each of the anchors 420 includes a platform 424 that is substantially wider than the platform 24 of the anchor 20 in the first embodiment of FIGS. 1–7. The platform 424 has a cylindrical outer surface 426 that extends between oppositely disposed first and second end surfaces 428 and 430. An attachment tab 440 projects axially away from the first end surface 428 of the platform 424. The attachment tab 440 includes a pair of oppositely disposed planar surfaces 442 and a pair of oppositely disposed arcuate surfaces 444.

The attachment tabs 440 provide structure for connecting spinal fixation instrumentation to each of the platforms 424 and for driving the anchors 420. The second end surface 430 of the platform 424 of each anchor 420 has a shape that is complimentary to the shape of an upper or lower surface of a vertebrae. The second end surface 430 of the platform 424 may be porous, pitted, or have a biocompatible surface coating to assist with fixation of the anchors 420 to the vertebrae.

Similar to the anchor 20 in the first embodiment of FIGS. 1–7, the anchors 420 have first and second helical spikes 450 and 452 that project from the second end surface 430 of the platform 424. The spikes 450 and 452 extend around the axis 422 and have a conical shape that increases in diameter as the helical spikes extend away from the platform 424. It should be understood that the anchors 420 could alternatively have three helical spikes as shown in the second embodiment of FIGS. 9–13. Although the outer surfaces of the helical spikes 450 and 452 are shown as being smooth in FIGS. 14–17, it is contemplated that the outer surfaces may instead be porous, pitted, or have a biocompatible coating to assist with fixation of the anchors 420 to the vertebrae.

As shown in FIGS. 16 and 17, each of the helical spikes 450 and 452 has a solid cross-section. Alternatively, each of the helical spikes 450 and 452 could have a tubular cross-section as shown in FIGS. 16A and 17A. It is also contemplated that the modified configurations of the helical spikes 50' and 52' illustrated in FIGS. 32–35 could also be applied to the third embodiment of FIGS. 14–17. Specifically, the connecting portions and/or the tip portions of the helical spikes 450 and 452 could have a solid cross-section, while the intermediate portions have a tubular cross-section. Such modified configurations of the anchors 420 provide additional means for matching the modulus of elasticity of the bone and allow the surgeon to select a particular configuration based on the specific surgical application and quality of the bones in which the anchors are to be implanted.

The apparatus 410 according to the third embodiment of FIGS. 14–17 is particularly useful for a corpectomy application in which a damaged vertebrae is removed. As is shown in FIG. 14, after a portion of a damaged vertebrae 460 is removed, a first one of the pair of anchors 420 is implanted into a vertebrae 462 directly above the removed vertebrae 460 and a second one of the pair of anchors 420 is implanted into a vertebrae 464 directly below the removed vertebrae.

The anchors 420 are also made of a shape memory alloy and are implanted in the vertebrae 462 and 464 in the same manner as the anchor 20 according to the first embodiment of FIGS. 1–7. The shapes of the anchors 420 at various stages of the implantation process are similar to that which is illustrated in FIGS. 7A–7C for the anchor 20 of the first embodiment. Hence, the shape that is "memorized" into the material of the anchors 420 is illustrated in FIG. 14.

The anchors 420 has a first condition (not shown) prior to implantation in the vertebrae 462 and 464 in which the helical spikes 450 and 452 do not have a conical shape, but instead have a generally cylindrical shape with a first maximum diameter. In addition, in the first condition, the helical spikes 450 and 452 have a first axial length. In order for the anchors 420 to take the shape of the first condition, the temperature of the anchors must be below the TTR of the material so that the material is soft and ductile. As with the anchor 20 of the first embodiment, each of the anchors 420 is moved into the first condition using the tubular sleeve 70 illustrated in FIGS. 7A–7C.

To return the helical spikes 450 and 452 to the conical shape as they emerge from the sleeve 70, heat is applied to each anchor 420 until the temperature of the anchor exceeds the TTR for the shape memory material. With the helical spikes 450 and 452 expanding radially and contracting axially as they emerge from the sleeve 70, the helical spikes are implanted in a respective one of the vertebrae 462 and 464 in the conical shape, or second condition, as illustrated in FIG. 7C for the first embodiment. In the implanted second condition, the helical spikes 450 and 452 have a second maximum diameter that is larger than the first maximum diameter of the helical spikes in the first condition. Further, in the implanted second condition, the helical spikes 450 and 452 have a second axial length that is smaller than the first axial length of the helical spikes in the first condition.

It is contemplated that the first and second conditions of the helical spikes 450 and 452 described above could be achieved even if only certain portions of the helical spikes were made from a shape memory alloy. For example, it is contemplated that the tip portions and the intermediate portions of the helical spikes 450 and 452 could be made from a shape memory alloy, while the connecting portions are made from another biocompatible metal. Further, if a shape memory material is not used at all in the helical spikes 450 and 452 and a material such as spring steel is used instead, the helical spikes would still be able to be compressed into the first condition and expand into the second condition upon implantation.

The anchors 420 are implanted so that they extend co-linearly along the axis 422. When implanted, the helical spikes 450 and 452 of the anchor 420 in the vertebrae 462 extend in an upward direction from the platform 430 of the upper (as viewed in FIGS. 14 and 15) anchor, while the helical spikes 450 and 452 of the other anchor in the vertebrae 464 extend in a downward direction from the platform 430 of the lower (as viewed in FIGS. 14 and 15) anchor.

A spinal fixation implant in the form of a cylinder member 480 connects the pair of anchors 420 to structurally support the vertebral column in the absence of the removed vertebrae 460. The cylinder member 480 has a cylindrical outer surface 482 and an eccentric inner surface 484. The cylinder member 480 has a first slot 486 at a first end 488 and a second slot 490 at a second end 492. The first and second slots 486 and 490 receive the attachment tabs 440 on the anchors 420 and allow the cylinder member 480 to be inserted between the anchors. Once inserted between the anchors 420, the cylinder member 480 is then rotated relative to the anchors about the axis 422. Rotation of the cylinder member 480 brings the arcuate surfaces 444 on the attachment tabs 440 of the anchors 420 into frictional engagement with the eccentric inner surface 484 of the cylinder member, thereby securing the cylinder member.

As with the previous embodiments, the conical shape of the helical spikes 450 and 452 according to the third embodiment makes the anchors 420, when implanted, highly resistant to being pulled out of the vertebrae 462 and 464 and to toggling in the vertebrae despite being subjected to substantial forces caused by human body movement and muscle memory. As mentioned previously, the conical shape of the helical spikes 450 and 452 increases the amount of surface area engaged by the anchor 420, distributes any load on the anchor, and provides fixation over a larger volume of bone. Further, because the helical spikes 450 and 452 of the anchors 420 displace relatively little of the cancellous bone of the vertebrae during implantation, a relatively small amount of torque is required to implant the anchors in the vertebrae. Moreover, because the helical spikes 450 and 452 displace only a small amount of bone, the helical spikes do not create a core defect that could lead to bone destruction or failure, such as the helical spikes pulling out of the vertebrae. Finally, the use of a shape memory alloy for the helical spikes 450 and 452 allows the anchors 420 to have a smaller diameter prior to implantation, which permits minimally invasive endoscopic surgery through a cannula, and a wider diameter when implanted, which improves fixation in a vertebrae.

Figure 18:
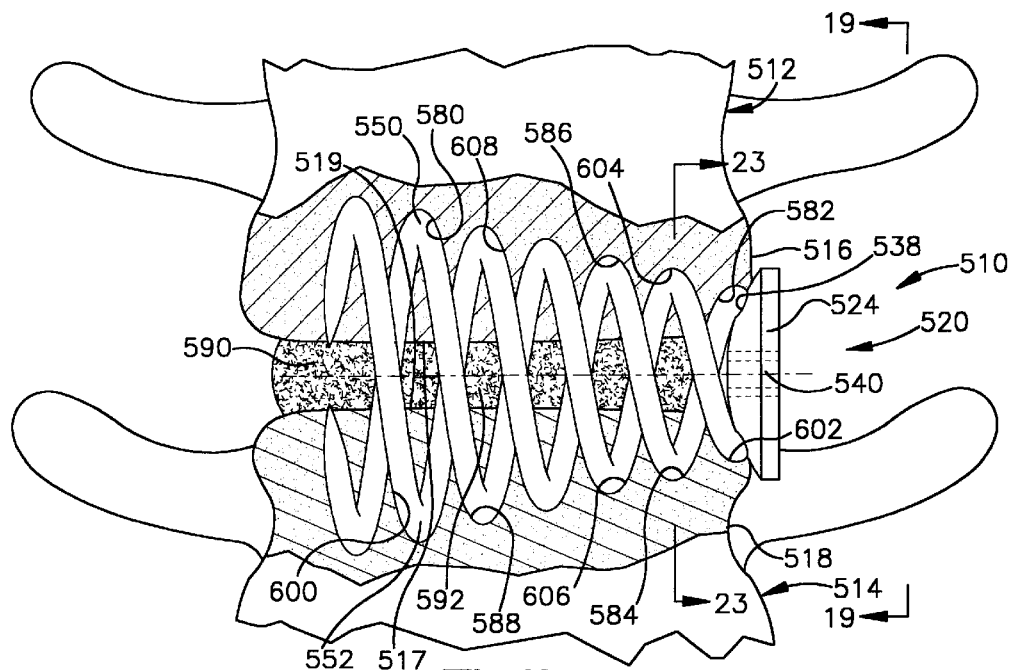
FIG. 18 is a schematic anterior view of an apparatus implanted in an adjacent pair of vertebral bodies in accordance with a fourth embodiment of the present invention.

FIGS. 18–24 illustrate an apparatus 510 constructed in accordance with a fourth embodiment of the present invention. The fourth embodiment of the present invention is particularly directed to an apparatus for attaching and stabilizing adjacent vertebral bodies while the vertebral bodies fuse together. As representative of the fourth embodiment, FIG. 18 illustrates the apparatus 510 implanted into an adjacent pair of lumbar vertebrae 512 and 514 in a vertebral column (not shown). It should be understood that the apparatus 510 could be implanted into any adjacent pair of vertebrae. The vertebrae 512 has a side surface 516 and a lower surface (or end plate) 517 (FIG. 18). The vertebrae 514 has a side surface 518 and an upper surface (or end plate) 519.

The apparatus 510 comprises an interbody stabilizer 520 made from a biocompatible material. Known biocompatible materials include titanium, stainless steel, and spring steel. It is contemplated that the biocompatible material used for the anchor 20 could be polymeric or composite in nature. In accordance with one feature of the present invention, the interbody stabilizer 520 is at least partially made from a shape memory alloy as described above with regard to the first embodiment of FIGS. 1–7.

The interbody stabilizer 520 is centered about a longitudinal axis 522 (FIG. 20). The interbody stabilizer 520 includes a platform 524 having a generally cylindrical outer surface 526 extending between oppositely disposed first and second ends 528 and 530. The second end 530 of the platform 524 includes an end surface 538 that extends transverse to the side surfaces 516 and 518 of the adjacent vertebrae 512 and 514, respectively. The end surface 538 of the platform 524 has a shape that is complimentary to the side surfaces 516 and 518 of the vertebrae 512 and 514, respectively. The end surfaces 538 of the platform 524 may be porous, pitted, or have a biocompatible surface coating to assist with fixation of the interbody stabilizer to the vertebrae 512 and 514.

The platform 524 of the interbody stabilizer 520 further includes an axial passage 540 that extends from the first end 528 to the end surface 538. The passage 540 has a hexagonal configuration for receiving a rotatable driver (not shown).

First and second helical spikes 550 and 552 project from the end surface 538 of the platform 524. The helical spikes 550 and 552 resemble a pair of intertwined corkscrews, both of which have a conical shape that increases in diameter as the helical spikes extend away from the platform 524. As shown in FIGS. 21 and 22, each of the helical spikes 550 and 552 has a solid cross-section. Alternatively, each of the helical spikes 550 and 552 could have a tubular cross-section, as illustrated in FIGS. 21A and 22A, which provides a means for matching the modulus of elasticity of the bone.

According to the fourth embodiment illustrated in FIGS. 18–24, the first and second helical spikes 550 and 552 extend symmetrically around the axis 522. The spikes 550 and 552 extend in a conical pattern. It is contemplated, however, that the conical shape of the first and second helical spikes 550 and 552 could be different from each other (i.e., one spike being a smaller cone than the other).

In the fourth embodiment of FIGS. 18–24, the first and second helical spikes 550 and 552 have the same axial length, and also have the same cross-sectional shape. It is contemplated, however, that the first and second helical spikes 550 and 552 could have different axial lengths. Further, it is contemplated that the helical spikes 550 and 552 could have a different cross-sectional shape, such as an oval shape. It also contemplated that the first and second helical spikes 550 and 552 could have different diameters (i.e., one spike being thicker than the other spike). Finally, it is contemplated that the helical spikes 550 and 552 should have the same pitch, and that the pitch of the helical spikes would be selected based on the specific surgical application and quality of the bone in which the interbody stabilizer 520 is to be implanted.

Each of the first and second helical spikes 550 and 552 can be divided into three portions: a connecting portion 554, an intermediate portion 556, and a tip portion 558. The connecting portion 554 of each of the helical spikes 550 and 552 is located at a proximal end 560 that adjoins the end surface 538 of the platform 524. The connecting portion 554 may include barbs (not shown) for resisting pull-out of the helical spikes 550 and 552 from the vertebrae 512 and 514. According to one method for manufacturing the interbody stabilizer 520, the connecting portion 554 of each of the helical spikes 550 and 552 is fixedly attached to the platform 524 by inserting, in a tangential direction, the proximal ends 560 of the helical spikes into openings (not shown) in the end surfaces 38 and welding the connecting portions 554 to the platform. The inserted proximal ends 560 of the helical spikes 550 and 552 help to reduce bending stresses on the helical spikes under tensile or shear loads.

Figure 23:
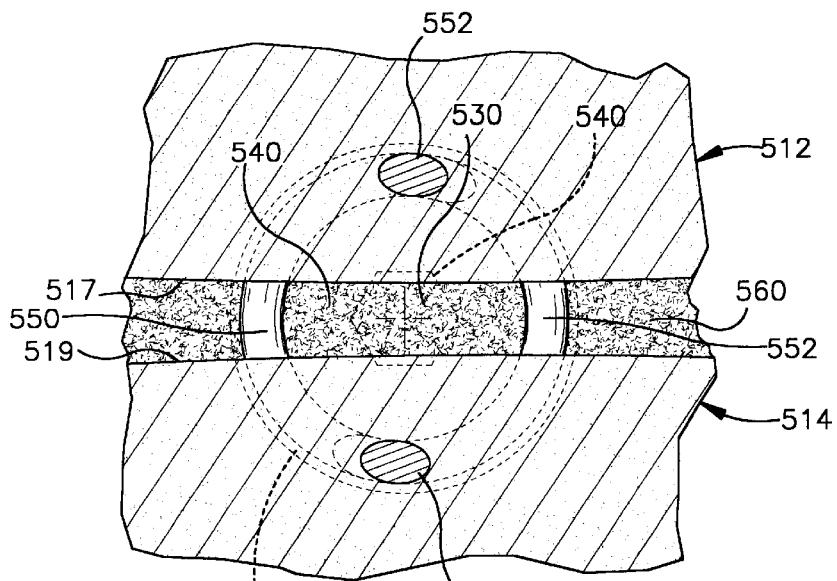
FIG. 23 is a sectional view taken along 23—23 in FIG. 18.

Alternatively, the helical spikes 550 and 552 may be formed integrally with the platform 524, such as by casting the interbody stabilizer 520. If the interbody stabilizer 520 is cast, it is contemplated that a fillet (not shown) may be added at the junction of the helical spikes 550 and 552 and the platform 524 to strengthen the junction and minimize stress concentrations at the connecting portions 554. The fillet at the junction of the helical spikes 550 and 552 and the platform 524 also helps to reduce bending stresses in the connecting portions 554 of the helical spikes under tensile or shear loads. As best seen in FIG. 23, the connecting portions 554 at the proximal ends 560 of the first and second helical spikes 550 and 552 are spaced 180° apart about the axis 522 to balance the interbody stabilizer 520 and evenly distribute loads on the helical spikes.

The tip portion 558 of each of the helical spikes 550 and 552 is located at a distal end 562 of the helical spikes. The intermediate portion 556 of each of the helical spikes 550 and 552 extends between the tip portion 558 and the connecting portion 554. The intermediate portion 556 and the tip portion 558 of each of the helical spikes 550 and 552 have a diameter that is less than or equal to the diameter of the connecting portions 554. If the diameter of the intermediate portions 556 and the tip portions 558 is less than the outer of the connecting portions 554, the increased thickness of the connecting portions 554 of the helical spikes 550 and 552 will help to provide the interbody stabilizer 520 with increased tensile strength at the junction of the helical spikes and the platform 524.

It is contemplated that the modified configurations of the helical spikes 50' and 52' illustrated in FIGS. 32–35 could also be applied to the fourth embodiment of FIGS. 18–24. Specifically, the connecting portions and/or the tip portions of the helical spikes 550 and 552 could have a solid cross-section, while the intermediate portions 556 have a tubular cross-section. Such modified configurations of the interbody stabilizer 520 provide additional means for matching the modulus of elasticity of the bone and allow the surgeon to select a particular configuration based on the specific surgical application and quality of the bone in which the interbody stabilizer is to be implanted.

Figure 25:
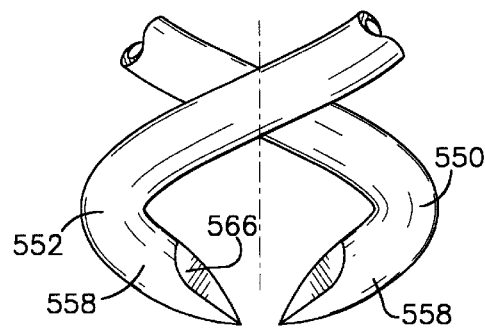
FIG. 25 illustrates an alternate configuration for an end portion of the apparatus of FIG. 20.

The tip portion 558 of each of the helical spikes 550 and 552 is self-penetrating and provides the helical spikes with the ability to penetrate into a respective one of the vertebrae 512 and 514 as the platform 524 of the interbody stabilizer 520 is rotated in a clockwise direction. The tip portions 558 illustrated in FIGS. 18–24 have an elongated conical shape with a sharp pointed tip 568. FIG. 25 illustrates an alternative, self-tapping configuration for the tip portions 558 which includes a planar surface 566 for driving into the vertebrae 512 and 514, in the same manner that a wood chisel turned upside-down drives into wood, as the platform 524 is rotated. It is contemplated that the tip portions 558 could also have a pyramid shape, similar to the tip of a nail. Although the outer surfaces of the helical spikes 550 and 552 are shown as being smooth in FIGS. 18–24, it is contemplated that the outer surfaces may instead be porous, pitted, or have a biocompatible coating to assist with fixation of the interbody stabilizer 520 to the vertebrae 512 and 514.

As mentioned previously, the interbody stabilizer 520 is made from a shape memory alloy, which allows the interbody stabilizer to have more than one shape. FIGS. 24A–24C illustrate the shapes of the interbody stabilizer 520 at various stages of the implantation process. The shape that is "memorized" into the material of the interbody stabilizer 520 is illustrated in FIGS. 18–20 and 34C. FIG. 24A illustrates the interbody stabilizer 520 in a first condition prior to implantation into the adjacent vertebrae 512 and 514. In the first condition, the helical spikes 550 and 552 of the interbody stabilizer 520 do not have a conical shape, but instead have a generally cylindrical shape with a uniform maximum diameter D1. Further, in the first condition, the helical spikes 550 and 552 have an axial length L1. In order for the interbody stabilizer 520 to take the shape of the first condition, the temperature of the interbody stabilizer must be below its TTR so that the material of the interbody stabilizer is soft and ductile.

As in the first embodiment, the interbody stabilizer 520 is moved into the first condition of FIG. 24A with the aid of the tubular sleeve 70. The internal threads 72 inside the sleeve 70 mate with the helical spikes 550 and 552 of the interbody stabilizer 520 to aid in drawing the helical spikes into the sleeve upon rotation of the interbody stabilizer. With the temperature of the interbody stabilizer 520 below its TTR, the interbody stabilizer is pulled into the sleeve 70 by rotating the platform 524 in a first direction with a driver (not shown). As the helical spikes 550 and 552 are drawn into the sleeve 70, the helical spikes are compressed radially inward, causing their axial length to grow to the axial length L1.

FIG. 24B illustrates the interbody stabilizer 520 during implantation into the adjacent pair of vertebrae 512 and 514. As shown in FIG. 24B, the helical spikes 550 and 552 emerge from the sleeve 70 when the platform 524 is rotated in a second direction that is opposite the first direction. As the helical spikes 550 and 552 emerge from the sleeve 70, it is desired that the helical spikes return to the memorized conical shape of FIG. 20. To return the helical spikes 550 and 552 to the conical shape as they emerge from the sleeve 70, heat is applied to the interbody stabilizer 520 until the temperature of the interbody stabilizer exceeds the TTR for the shape memory material. Simple body temperature may be sufficient to raise the temperature of the anchor 520 above its TTR. If additional heat is needed, heat may be applied in many ways, such as passing electric current through a wire connected with the interbody stabilizer 520 or the sleeve 70, transmitting radio waves that inductively heat the interbody stabilizer, or applying a hot saline pack to the sleeve.

With the helical spikes 550 and 552 expanding radially, but contracting axially, as they emerge from the sleeve 70, the helical spikes are implanted in the vertebrae 512 and 514 in the conical shape, or second condition, illustrated in FIG. 24C. As shown in FIG. 24C, in the implanted second condition, the helical spikes 550 and 552 have a maximum diameter D2 that is larger than the maximum diameter D1 of the helical spikes in the first condition. Further, in the implanted second condition, the helical spikes 550 and 552 have an axial length L2 that is smaller than the axial length of the helical spikes in the first condition.

It is contemplated that the first and second conditions of the helical spikes 550 and 552 described above could be achieved even if only certain portions of the helical spikes were made from a shape memory alloy. For example, it is contemplated that the tip portions 558 and the intermediate portions 556 of the helical spikes 550 and 552 could be made from a shape memory alloy, while the connecting portions 54 are made from another biocompatible metal. Further, it should be understood that if a shape memory material is not used at all in the helical spikes 550 and 552 and a material such as spring steel is used instead, the helical spikes would still be able to be compressed in to the first condition of FIG. 24A, and expand into the second condition upon implantation as shown in FIGS. 24B and 24C.

Figure 19:
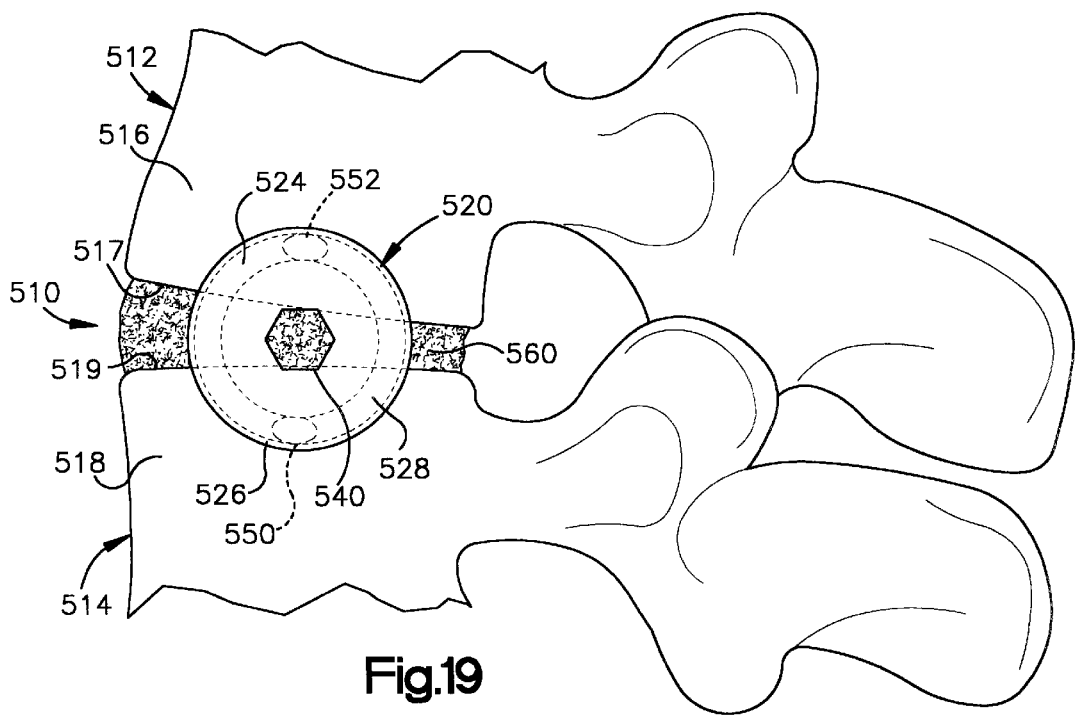
FIG. 19 is an end view taken along line 19—19 in FIG. 18.

Turning now to a more detailed discussion of the procedure for implanting the interbody stabilizer 520, FIGS. 18 and 19 illustrate the interbody stabilizer 520 implanted in the adjacent lumbar vertebrae 512 and 514 to stabilize the vertebrae. First, disk material that normally separates the vertebrae 512 and 514 is removed by the surgeon. Removal of the disk material leaves an interbody space 560 (FIG. 19) between the vertebrae 512 and 514. A tool (not shown) is then used to punch a hole (not shown) in the cortical bone (not shown) of each of the vertebrae 512 and 514. The hole in the vertebrae 512 may be punched in either the side surface 516 or the lower surface 517. The hole in the vertebrae 514 may be punched in either the side surface 518 or the upper surface 519. The holes in the vertebrae 512 and 514 are punched in locations that correspond to the spacing of the tip portions 558 of the helical spikes 550 and 552 of the interbody stabilizer 520. The holes in the vertebrae 512 and 514 are intended to make the initial rotation of the stabilizer 520 easier. It should be noted that one or both of the configurations of the tip portions 558 illustrated in FIGS. 18–24 and FIG. 25 may be able to punch through the cortical bone upon rotation of the interbody stabilizer 520, thus eliminating the need for the aforementioned tool to punch holes in the cortical bone.

The tip portions 558 of the interbody stabilizer 520 are placed in the holes in the vertebrae 512 and 514 and a rotatable driver (not shown) is inserted into the passage 540 in the platform 524. The helical spikes 550 and 552 are then heated, as discussed above, to a temperature above the TTR for the shape memory material. The driver is then rotated, causing the interbody stabilizer 520 to rotate as well.

Rotation of the interbody stabilizer 520 screws the helical spikes 550 and 552 into the vertebrae 512 and 514, respectively. The tangentially-oriented connection between the connection portions 554 of the helical spikes 550 and 552 and the platform 524, as well as the constraining function of the sleeve 70, minimizes bending loads on the connecting portions during rotation of the interbody stabilizer 520. Further, the tangentially-oriented connection ensures that the force vector resulting from axial force torque and applied by the driver to the platform 524 is transmitted along the helical centerline (not shown) of each of the helical spikes 550 and 552.

As the interbody stabilizer 520 is rotated, the tip portion 558 of the first helical spike 550 penetrates the cancellous bone in the vertebrae 512 and cuts a first helical segment 582 of a first conical tunnel 580 (FIG. 18) in the vertebrae 512. Simultaneously, the tip portion 558 of the second helical spike 552 penetrates the cancellous bone of the vertebrae 514 and cuts a first helical segment 602 of a second conical tunnel 600 in the vertebrae 514.

At some point between 90° and 180° of rotation of the interbody stabilizer 520, the tip portions 558 of the helical spikes 550 and 552 penetrate back out of the vertebrae 512 and 514, respectively and into the interbody space 560. More specifically, the tip portion 558 of the first helical spike 550 projects through the lower surface 517 of the vertebrae 512 and into the interbody space 560. Simultaneously, the tip portion 558 of the second helical spike 552 projects through the upper surface 519 of the vertebrae 514 and into the interbody space 560.

As the interbody stabilizer 520 is rotated beyond 180°, the tip portions 558 of the helical spikes 550 and 552 move through the interbody space 560 and engage the vertebrae 514 and 512, respectively. The tip portion 558 of the first helical spike 550 penetrates into the upper surface 519 of the vertebrae 514, while the tip portion 558 of the second helical spike 552 projects through the lower surface 517 of the vertebrae 512. Continued rotation of the interbody stabilizer 520 causes the tip portion. 558 of the first helical spike 550 to cut a second helical segment 584 of the first conical tunnel 580 in the vertebrae 514. Similarly, the continued rotation causes the tip portion 558 of the second helical spike 552 to cut a second helical segment 604 of the second conical tunnel 600 in the vertebrae 512.

After another 90° to 180° of rotation of the interbody stabilizer 520, the tip portions 558 of the helical spikes 550 and 552 penetrate back out of the vertebrae 514 and 512, respectively, and into the interbody space 560. More specifically, the tip portion 558 of the first helical spike 550 projects through the upper surface 519 of the vertebrae 514 and the tip portion 558 of the second helical spike 552 projects through the lower surface 517 of the vertebrae 512.

As the interbody stabilizer 520 is rotated further, the tip portions 558 of the helical spikes 550 and 552 move through the interbody space 560 and re-engage the vertebrae 512 and 514, respectively. The tip portion 558 of the first helical spike 550 penetrates the lower surface 517 of the vertebrae 512 and cuts a third helical segment 586 of the first conical tunnel 580 in the vertebrae 512. Simultaneously, the tip portion 558 of the second helical spike 552 penetrates the lower surface 519 of the vertebrae 514 and cuts a third helical segment 606 of the second conical tunnel 600 in the vertebrae 514.

After further rotation of the interbody stabilizer 520, the tip portions 558 of the helical spikes 550 and 552 again penetrate back out of the vertebrae 512 and 514, respectively and into the interbody space 560. The tip portion 558 of the first helical spike 550 projects through the lower surface 517 of the vertebrae 512, while the tip portion 558 of the second helical spike 552 projects through the upper surface 519 of the vertebrae 514. The interbody stabilizer 520 is then rotated so that the tip portions 558 of the helical spikes 550 and 552 move through the interbody space 560 and re-engage the vertebrae 514 and 512, respectively. The tip portion 558 of the first helical spike 550 again penetrates into the upper surface 519 of the vertebrae 514, causing the tip portion 558 of the first helical spike 550 to cut a fourth helical segment 588 of the first conical tunnel 580 in the vertebrae 514. Similarly, the tip portion 558 of the second helical spike 552 again penetrates through the lower surface 517 of the vertebrae 512, causing the tip portion 558 of the second helical spike 552 to cut a fourth helical segment 608 of the second conical tunnel 600 in the vertebrae 512.

This pattern of screwing the helical spikes 550 and 552 of the interbody stabilizer 520 into and out of each of the vertebrae 512 and 514 in an alternating manner continues with each revolution of the platform 524 by the driver. The continued rotation of the platform 524 embeds the helical spikes 550 and 552 of the interbody stabilizer 520 into the vertebrae 512 and 514 and attaches the interbody stabilizer to each of the vertebrae. With each rotation of the interbody stabilizer 520, the conical tunnels 580 and 600 enlarge radially and capture a larger volume of bone without further damage to the vertebrae. Thus, the connection between the interbody stabilizer and each of the vertebrae 512 and 514 gets stronger with each revolution of the interbody stabilizer 520. The attachment of the interbody stabilizer 520 to each of the vertebrae 512 and 514 thus fastens, or pins, the vertebrae together, yet spaced apart. Rotation of the platform 524 is terminated when the end surface 538 of the platform seats against one or both of the side surfaces 516 and 518 of the vertebrae 512 and 514, respectively.

Once the interbody stabilizer 520 is implanted, bone graft material 590 (shown schematically in FIGS. 18 and 23) for permanently fusing the vertebrae 512 and 514 is placed into the interbody space 560. More specifically, the bone graft material 590 is placed into a cavity 592 defined by the helical spikes 550 and 552, the lower surface 517 of the vertebrae 512, and the lower surface 519 of the vertebrae 514. The bone graft material 590, which may comprise bone chips and/or synthetic bone material, is placed into the cavity 592 through the axial passage 540 in the platform 524 of the interbody stabilizer 520. A sufficient amount of the bone graft material 590 is placed into the cavity 592 to fill not only the cavity, but also the entire interbody space 560.

When implanted, the interbody stabilizer 520 is attached to both of the vertebrae 512 and 514 and securely fastens the vertebrae together. Because each of the helical spikes 550 and 552 penetrates into and subsequently out of each of the vertebrae 512 and 514, the helical spikes provide multiple fixation locations between the interbody stabilizer 520 and the vertebrae that pin the vertebrae together. The interbody stabilizer 520 is therefore able to resist relative movement of the vertebrae 512 and 514 toward or away from each other, and does not rely on surrounding ligaments to stabilize the vertebrae. More specifically, the interbody stabilizer 520 resists relative movement of the vertebrae 512 and 514, through bending or rotation, along any one of the three planes of motion (sagittal, coronal, or horizontal). Thus, the interbody stabilizer 520 is able to maintain proper intervertebral spacing and provide effective stabilization of the adjacent vertebrae 512 and 514, despite substantial forces on the interbody stabilizer caused by human body movement and muscle memory, while the bone graft material 590 fuses the vertebrae together.

Advantageously, the conical shape of the helical spikes 550 and 552 increases the amount of surface area engaged by the interbody stabilizer 520, spreads any load on the interbody stabilizer out over different areas of the vertebrae 512 and 514, and provides fixation over a larger volume of bone. The aforementioned advantages of the conical shape of the helical spikes 550 and 552 are especially helpful when implanting the interbody stabilizer 520 in osteoporotic bone. Further, the interbody stabilizer 520 has a simple one-piece construct that does not require a large amount of torque to implant, and does not require substantial cutting of cortical bone (i.e., a reaming or tapping procedure) to prepare the vertebrae 512 and 514 to accept the interbody stabilizer. Thus, the interbody stabilizer 520 is not only a simplified construct, but also simplifies the steps required for implantation into adjacent vertebrae. Finally, the use of a shape memory alloy for the helical spikes 550 and 552 allows the interbody stabilizer 520 to have a smaller diameter prior to implantation, which permits minimally invasive endoscopic surgery through a cannula, and a wider diameter when implanted, which improves fixation in the adjacent vertebrae 512 and 514.

Figure 26:
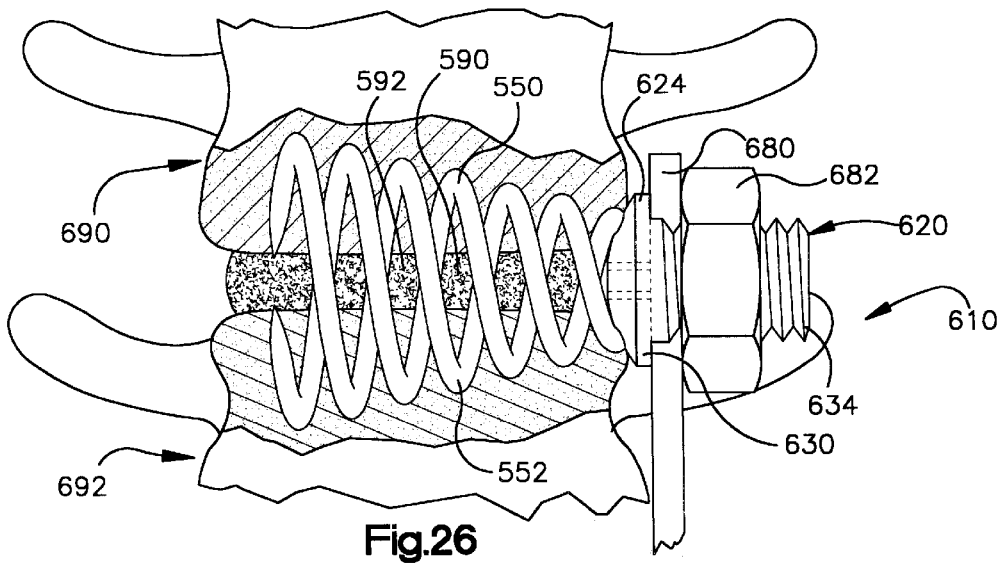
FIG. 26 is a schematic anterior view illustrating a fifth embodiment of the present invention.

FIG. 26 illustrates an apparatus 610 constructed in accordance with a fifth embodiment of the present invention. In the fifth embodiment of FIG. 26, reference numbers that are the same as those used in the fourth embodiment of FIGS. 18–24 designate parts that are the same as parts in the fourth embodiment.

According to the fifth embodiment, the apparatus 610 comprises an interbody stabilizer 620 having a platform 624. The platform 624 includes a generally rectangular slot (not numbered) that extends axially from an open end 628 of the platform toward an opposite end 630 of the platform. Adjacent the open end 628, the platform 624 includes first and second segments of external threads 634 (only one of which is shown) that are separated by the slot. The slot and the threads 634 provide structure for connecting spinal fixation instrumentation to the platform 624.

The first and second helical spikes 550 and 552 project from the end surface 538 at the second end 630 of the platform 624. The helical spikes 550 and 552 resemble a pair of intertwined corkscrews, both of which have a conical shape that increases in diameter as the helical spikes extend away from the platform 624.

The helical spikes 550 and 552 according to the fifth embodiment of FIG. 26 are also made of a shape memory alloy and are implanted in the vertebrae 512 and 514 in the same manner as the helical spikes of the interbody stabilizer 520 according to the fourth embodiment. The shapes of the interbody stabilizer 620 at various stages of the implantation process are identical to that which is illustrated in FIGS. 24A–24C for the interbody stabilizer 520 of the fourth embodiment. Hence, the shape that is "memorized" into the material of the interbody stabilizer 620 is illustrated in FIG. 26. Further, the interbody stabilizer 620 has a first condition (not shown) prior to implantation in a vertebrae in which the helical spikes 550 and 552 do not have a conical shape, but instead have a generally cylindrical shape with a first maximum diameter. In addition, in the first condition, the helical spikes 550 and 552 have a first axial length. In order for the interbody stabilizer 620 to take the shape of the first condition, the temperature of the anchor must be below its TTR so that the material of the anchor is soft and ductile. As in the fourth embodiment, the interbody stabilizer 620 is also moved into the first condition with the aid of the tubular sleeve 70 shown in FIGS. 24A–24C.

To return the helical spikes 550 and 552 to the conical shape as they emerge from the sleeve 70, heat is applied to the interbody stabilizer 620 until the temperature of the anchor exceeds the TTR for the shape memory material. With the helical spikes 550 and 552 expanding radially and contracting axially as they emerge from the sleeve 70, the helical spikes are implanted in a vertebrae in the conical shape, or second condition, as illustrated in FIG. 24C for the fourth embodiment. In the implanted second condition, the helical spikes 550 and 552 have a second maximum diameter that is larger than the first maximum diameter of the helical spikes in the first condition. Further, in the implanted second condition, the helical spikes 550 and 552 have a second axial length that is smaller than the first axial length of the helical spikes in the first condition.

FIG. 26 illustrates how the interbody stabilizer 620 may be used for segmental spinal fixation. Lumbar vertebrae L3 and L4, indicated by reference numbers 690 and 692, respectively, are shown in FIG. 26. Once the interbody stabilizer 620 is implanted, spinal fixation instrumentation such as a beam 680 which has been bent into a desired shape by the surgeon, is placed into the slot in the interbody stabilizer. A nut 682 is then screwed onto the threads 634 on the platform 624 and tightened to secure the beam 680 to the interbody stabilizer 620.

The interbody stabilizer 620 fastens the vertebrae 690 and 692 together and stabilizes the vertebrae until the bone graft material 590 placed in the cavity 592 defined inside each of the interbody stabilizers fuses the vertebrae. The beam 680 helps to achieve and maintain correction of spinal alignment and further support the vertebrae 690 and 692 until the vertebrae fuse together.

When implanted, the interbody stabilizer 620 is attached to both of the vertebrae 690 and 692 and securely fastens the vertebrae together. Because each of the helical spikes 550 and 552 penetrates into and subsequently out of each of the vertebrae 690 and 692, the helical spikes provide multiple fixation locations between the interbody stabilizer 620 and the vertebrae that pin the vertebrae together. The interbody stabilizer 620 is thus able to maintain proper intervertebral spacing and provide effective stabilization of the adjacent vertebrae 690 and 692, despite substantial forces on the interbody stabilizer caused by human body movement and muscle memory, while the bone graft material 590 fuses the vertebrae together. As mentioned previously, the conical shape of the helical spikes 550 and 552 increases the amount of surface area engaged by the interbody stabilizer 520, distributes any load on the interbody stabilizer, and provides fixation over a larger volume of bone. Finally, the use of a shape memory alloy for the helical spikes 550 and 552 allows the interbody stabilizers 520 to have a smaller diameter prior to implantation, which permits minimally invasive endoscopic surgery through a cannula, and a wider diameter when implanted, which improves fixation in the adjacent vertebrae 690 and 692.

FIGS. 27–31 illustrate an apparatus 710 constructed in accordance with a sixth embodiment of the present invention. In the sixth embodiment of FIGS. 27–31, reference numbers that are the same as those used in the fourth embodiment of FIGS. 18–24 designate parts that are the same as parts in the fourth embodiment.

According to the sixth embodiment, the apparatus 710 comprises an interbody stabilizer 720 having three helical spikes 730, 731, and 732 projecting tangentially from the end surface 538 of the platform 524. The spikes 730–732 are centered about the axis 522 and have a conical shape that increases in diameter as the helical spikes extend away from the platform. As shown in FIGS. 29–31, each of the helical spikes 730–732 has a solid cross-section. Alternatively, each of the helical spikes 730–732 could have a tubular cross-section as shown in FIGS. 29A–31A.

As shown in FIG. 26, the connecting portions 554 at the proximal ends 560 of the helical spikes 730–732 are spaced 120° apart about the axis 522, which balances the interbody stabilizer 720 and evenly distributes loads on the helical spikes. As in the fourth embodiment of FIGS. 18–24, in the sixth embodiment of FIGS. 27–31, the diameter of the connecting portions 554 of the helical spikes 730–732 is greater than or equal to the diameter of the intermediate portions 556 and the tip portions 558 of the helical spikes.

The three helical spikes 730–732 extend symmetrically in a conical pattern about the axis 522. It is contemplated, however, that the conical shape of one or more of the helical spikes 730–732 could be different from the other(s) (i.e., one spike being a smaller cone than the others). As shown in FIG. 27, the three helical spikes 730–732 have the same axial length and also have the same tubular cross-sectional shape. It is contemplated, however, that one or more of the helical spikes 730–732 could have different axial lengths. Further, it is contemplated that one or more of the helical spikes 730–732 could have a different cross-sectional shape, such as an oval shape. It also contemplated that the one or more of the helical spikes 730–732 could have different diameters (i.e., one spike being thicker or thinner than the other spike(s)). Finally, it is contemplated that the helical spikes 730–732 should have the same pitch, and that the pitch of the helical spikes would be selected based on the specific surgical application and quality of the bone in which the interbody stabilizer 720 is to be implanted.

It is contemplated that the modified configurations of the helical spikes 50' and 52' illustrated in FIGS. 32–35 could also be applied to the sixth embodiment of FIGS. 27–31. Specifically, the connecting portions and/or the tip portions of the helical spikes 730 and 732 could have a solid cross-section, while the intermediate portions 556 have a tubular cross-section. Such modified configurations of the interbody stabilizer 720 provide additional means for matching the modulus of elasticity of the bone.

The tip portion 558 of each of the helical spikes 730–732 illustrated in FIG. 27 has an elongated conical shape for penetrating into a vertebrae as the platform 524 of the interbody stabilizer 720 is rotated in the clockwise direction. It should be understood that the tip portions 558 of the helical spikes 730–732 of the interbody stabilizer 720 could alternatively be configured like the tip portions illustrated in FIG. 25. Although the outer surfaces of the helical spikes 730–732 are shown as being smooth in FIGS. 27–31, it is contemplated that the outer surfaces may instead be porous, pitted, or have a biocompatible coating to assist with fixation of the interbody stabilizer 720 to the vertebrae.

The helical spikes 730–732 of the interbody stabilizer 220 according to the sixth embodiment of FIGS. 27–31 are also made of a shape memory alloy and are implanted in a vertebrae in the same manner as the interbody stabilizer 520 according to the fourth embodiment. The shapes of the interbody stabilizer 220 at various stages of the implantation process are similar to that which is illustrated in FIGS. 24A–24C for the interbody stabilizer 520 of the fourth embodiment. Hence, the shape that is "memorized" into the material of the interbody stabilizer 720 is illustrated in FIG. 27. Further, the interbody stabilizer 220 has a first condition (not shown) prior to implantation in a vertebrae in which the helical spikes 730–732 do not have a conical shape, but instead have a generally cylindrical shape with a first maximum diameter. In addition, in the first condition, the helical spikes 730–732 have a first axial length. In order for the interbody stabilizer 720 to take the shape of the first condition, the temperature of the interbody stabilizer must be below its TTR so that the material of the interbody stabilizer is soft and ductile. As in the fourth embodiment, the interbody stabilizer 720 is also moved into the first condition with the aid of the tubular sleeve 70 illustrated in FIGS. 24A–24C.

To return the helical spikes 730–732 to the conical shape as they emerge from the sleeve 70, heat is applied to the interbody stabilizer 720 until the temperature of the interbody stabilizer exceeds the TTR for the shape memory material. With the helical spikes 730–732 expanding radially and contracting axially as they emerge from the sleeve 70, the helical spikes are implanted in a vertebrae in the conical shape, or second condition, as illustrated in FIG. 24C for the fourth embodiment. In the implanted second condition, the helical spikes 730–732 have a second maximum diameter that is larger than the first maximum diameter of the helical spikes in the first condition. Further, in the implanted second condition, the helical spikes 730–732 have a second axial length that is smaller than the first axial length of the helical spikes in the first condition.

It is contemplated that the first and second conditions of the helical spikes 730–732 described above could be achieved even if only certain portions of the helical spikes were made from a shape memory alloy. For example, it is contemplated that the tip portions 558 and the intermediate portions 556 of the helical spikes 730–732 could be made from a shape memory alloy, while the connecting portions 554 are made from another biocompatible metal. Further, if a shape memory material is not used at all in the helical spikes 730–732 and a material such as spring steel is used instead, the helical spikes would still be able to be compressed into the first condition and expand into the second condition upon implantation.

The interbody stabilizer 720 according to the sixth embodiment of FIGS. 27–31 is implanted into an adjacent pair of vertebrae in the same manner as the interbody stabilizer 720 according to the fourth embodiment. Further, the interbody stabilizer 720 according to the sixth embodiment may also be used to mount spinal fixation instrumentation as shown in the fifth embodiment of FIG. 26. When implanted, the interbody stabilizer 720 is attached to both of the adjacent vertebrae and fastens the vertebrae together. Further, the interbody stabilizer 720 maintains proper intervertebral spacing and provides effective stabilization of the adjacent vertebrae while the bone graft material placed in the cavity in the interbody stabilizer fuses the vertebrae together. Advantageously, the interbody stabilizer 720 is a simple one-piece construct that does not require a large amount of torque to implant and does not require substantial cutting of cortical bone (i.e., a reaming or tapping procedure) to prepare the adjacent vertebrae to accept the interbody stabilizer. The conical shape of the helical spikes 730–732 increases the amount of surface area engaged by the interbody stabilizer 720, distributes any load on the interbody stabilizer, and provides fixation over a larger volume of bone. Finally, the use of a shape memory alloy for the helical spikes 730–732 allows the anchor 720 to have a smaller diameter prior to implantation, which permits minimally invasive endoscopic surgery through a cannula, and a wider diameter when implanted, which improves fixation in a vertebrae.

FIG. 36 illustrates a cervical application of the apparatus 510 of FIG. 18 in accordance with the present invention. In FIG. 36, reference numbers that are the same as those used in the fourth embodiment of FIGS. 18–24 designate parts that are the same as parts in the fourth embodiment.

As shown in FIG. 36, the interbody stabilizer 520 has the first and second helical spikes 550 and 552 made from a shape memory alloy. The interbody stabilizer 520 is implanted into two cervical vertebrae 912 and 914 in the same manner as described above regarding the fourth embodiment of FIGS. 18–24. The end surface 538 of the interbody stabilizer 520 seats against anterior surfaces 916 and 918 of the vertebrae 912 and 914, respectively. As in the third embodiment, the interbody stabilizer 520 fastens the vertebrae 912 and 914 and stabilizes the vertebrae until the bone graft material 590 placed in the cavity 592 in the interbody stabilizer fuses the vertebrae. As mentioned previously, the conical shape of the helical spikes 550 and 552 increases the amount of surface area engaged by the interbody stabilizer 520, distributes any load on the interbody stabilizer, and provides fixation over a larger volume of bone. The use of a shape memory alloy for the helical spikes 550 and 552 allows the interbody stabilizer 520 to have a smaller diameter prior to implantation, which permits minimally invasive endoscopic surgery through a cannula, and a wider diameter when implanted, which improves fixation in a vertebrae.

Figure 38:
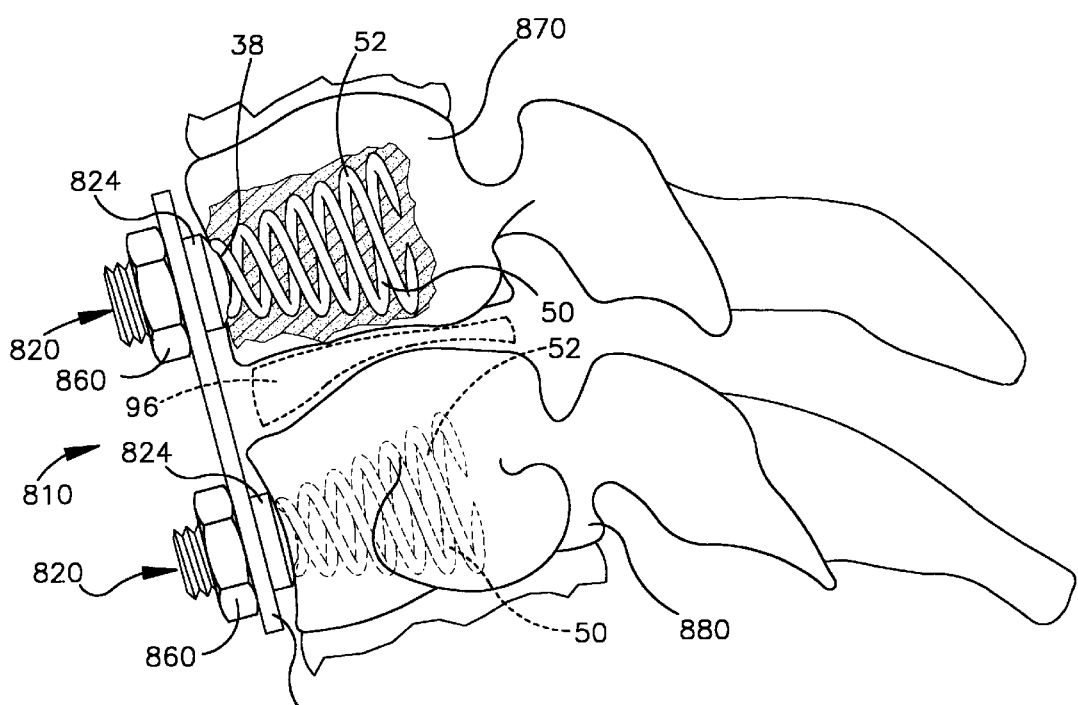
FIG. 38 is a schematic view of the apparatus of FIG. 37 implanted in cervical vertebrae.

FIGS. 37 and 38 illustrate an apparatus 810 constructed in accordance with a seventh embodiment of the present invention. In the seventh embodiment of FIGS. 37 and 38, reference numbers that are the same as those used in the first embodiment of FIGS. 1–7 designate parts that are the same as parts in the first embodiment.

According to the seventh embodiment, the apparatus 810 comprises an anchor 820 having a platform 824. The platform 824 has a threaded outer surface 830 adjacent a first end portion 832 and a cylindrical outer surface 840 adjacent a second end portion 842. The first end portion 832 of the platform 824 further includes an axial recess 834. The recess 834 has a hexagonal configuration for receiving a tool (not shown) for drivingly rotating the anchor 820. The first and second helical spikes 50 and 52 have a solid cross-section and project from the end surface 38 of the platform 824.

The anchor 820 is made of a shape memory alloy and is implanted in a vertebrae in the same manner as the anchor 20 according to the first embodiment of FIGS. 1–7. The shape of the anchor 820 at various stages of the implantation process is similar to that which is illustrated in FIGS. 7A–7C for the anchor 20 of the first embodiment. Hence, the shape that is "memorized" into the material of the anchor 820 is illustrated in FIG. 37.

The anchor 820 has a first condition (not shown) prior to implantation in the vertebrae in which the helical spikes 50 and 52 do not have a conical shape, but instead have a generally cylindrical shape with a first maximum diameter. In addition, in the first condition, the helical spikes 50 and 52 have a first axial length. In order for the anchor 820 to take the shape of the first condition, the temperature of the anchors must be below the TTR of the material so that the material is soft and ductile. As in the first embodiment of FIGS. 1–7, the anchor 820 is also moved into the first condition with the aid of the tubular sleeve 70.

To return the helical spikes 50 and 52 to the conical shape as they emerge from the sleeve 70, heat is applied to the anchor 820 until the temperature of the anchor exceeds the TTR for the shape memory material. With the helical spikes 50 and 52 expanding radially and contracting axially as they emerge from the sleeve 70, the helical spikes are implanted in the vertebrae in the conical shape, or second condition, as illustrated in FIG. 7C for the first embodiment. In the implanted second condition, the helical spikes 50 and 52 have a second maximum diameter that is larger than the first maximum diameter of the helical spikes in the first condition. Further, in the implanted second condition, the helical spikes 50 and 52 have a second axial length that is smaller than the first axial length of the helical spikes in the first condition.

It is contemplated that the first and second conditions of the helical spikes 50 and 52 described above could be achieved even if only certain portions of the helical spikes were made from a shape memory alloy. For example, it is contemplated that the tip portions and the intermediate portions of the helical spikes 50 and 452 could be made from a shape memory alloy, while the connecting portions are made from another biocompatible metal. Further, if a shape memory material is not used at all in the helical spikes 50 and 52 and a material such as spring steel is used instead, the helical spikes would still be able to be compressed into the first condition and expand into the second condition upon implantation.

The apparatus 810 further includes a plate 850 and a nut 860. The plate 850 has a first opening 852 for receiving the portion of the platform 824 which has the threaded outer surface 830. The plate 850 has a second opening 854 for receiving a second anchor 820 (see FIG. 38) or other fixation instrumentation (not shown). When the anchor 820 is implanted in a vertebrae, the nut 860 screws onto the threaded outer surface 830 of the platform 824 to secure the plate 850 to the anchor 820.

FIG. 38 shows a pair of the anchors 820 implanted, in the manner discussed above, in two cervical vertebrae 870 and 880. The end surface 38 of each of the anchors 820 engages a respective anterior surface on each of the vertebrae 870 and 880. The plate 850 connects the anchors 820 to help support the vertebrae 870 and 880 and transfer loads between the vertebrae until bone graft material 890 fuses the vertebrae. Like the anchor 20 according to the first embodiment, the anchor 820 according to the seventh embodiment, when implanted in the vertebrae, is highly resistant to being pulled out of the vertebrae and to toggling in the vertebrae despite being subjected to substantial forces caused by human body movement and muscle memory. The conical shape of the helical spikes 50 and 52 increases the amount of surface area engaged by the anchor 820, distributes any load on the anchor, and provides fixation over a larger volume of bone. Further, the use of a shape memory alloy for the helical spikes 50 and 52 allows the anchor 820 to have a smaller diameter prior to implantation, which permits minimally invasive endoscopic surgery through a cannula, and a wider diameter when implanted, which improves fixation in a vertebrae.

Figure 39:
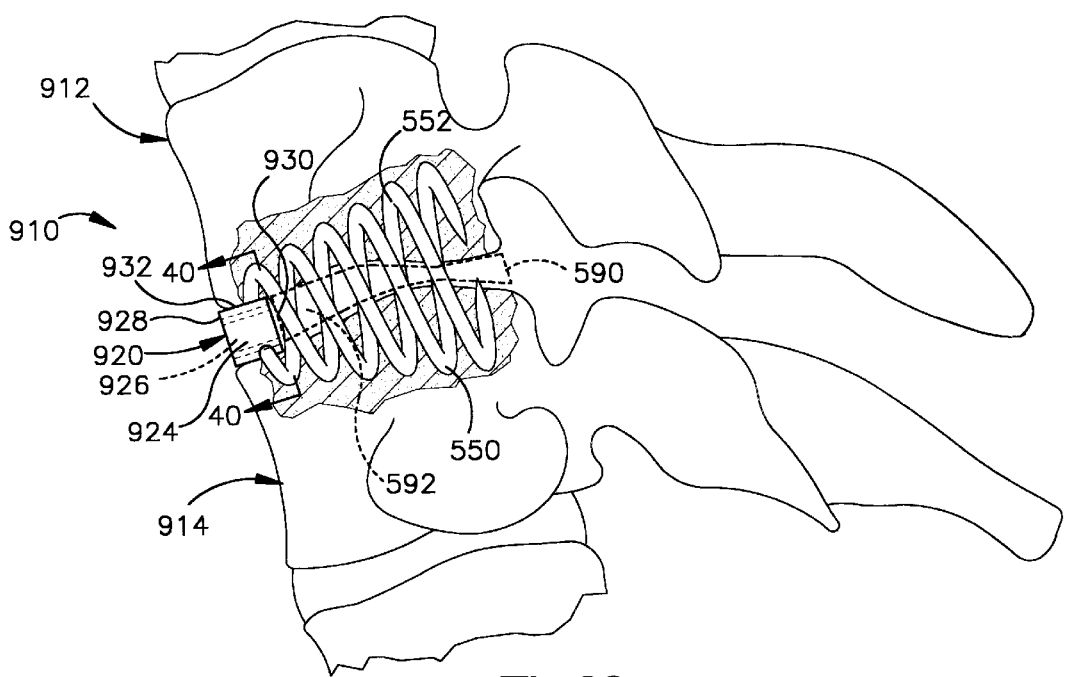
FIG. 39 is a sectional view illustrating an apparatus constructed in accordance with an eighth embodiment of the present invention.
Figure 40:
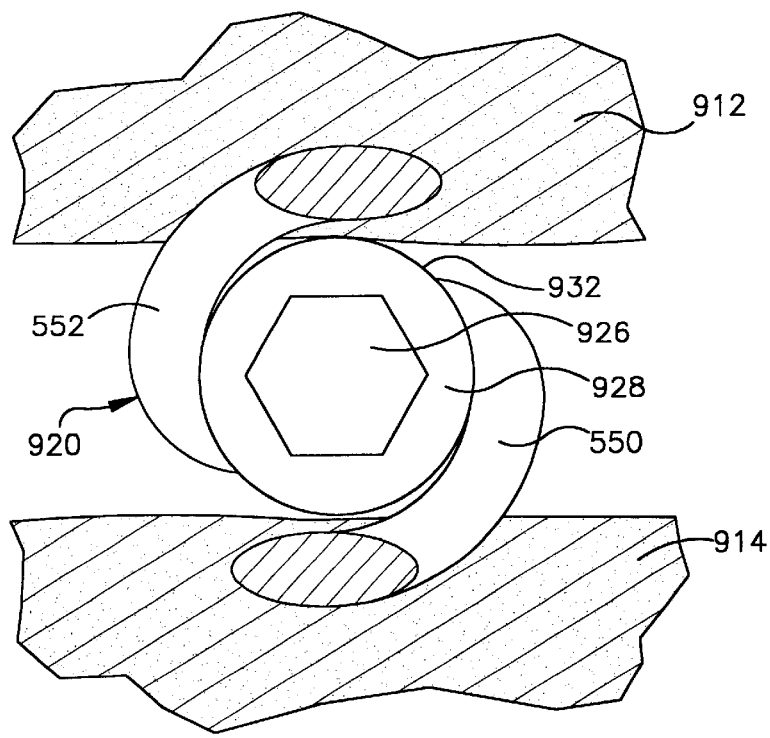
FIG. 40 is a sectional view taken along line 40—40 in FIG. 39.

FIGS. 39 and 40 illustrate an apparatus 910 constructed in accordance with an eighth embodiment of the present invention. In the eighth embodiment of FIGS. 39 and 40, reference numbers that are the same as those used in the fourth embodiment of FIGS. 18–24 designate parts that are the same as parts in the fourth embodiment.

According to the eighth embodiment, the apparatus 910 comprises an interbody stabilizer 920 having a platform 924. The platform 924 includes a hexagonal slot 926 that extends axially from an open end 928 of the platform toward an opposite end 930 of the platform. The platform 924 further includes a generally cylindrical outer surface 932 that extends from the open end 928 to the opposite end 930.

The first and second helical spikes 550 and 552 project tangentially from the cylindrical outer surface 932. The helical spikes 550 and 552 resemble a pair of intertwined corkscrews, both of which have a conical shape that increases in diameter as the helical spikes extend away from the platform 924.

The helical spikes 550 and 552 according to the eighth embodiment of FIGS. 39 and 40 are also made of a shape memory alloy and are implanted into an adjacent pair of vertebrae 912 and 914 in the same manner as the helical spikes of the interbody stabilizer 520 according to the fourth embodiment. The shapes of the interbody stabilizer 920 at various stages of the implantation process are identical to that which is illustrated in FIGS. 24A–24C for the interbody stabilizer 520 of the fourth embodiment. Hence, the shape that is "memorized" into the material of the interbody stabilizer 920 is illustrated in FIG. 39. Further, the interbody stabilizer 920 has a first condition (not shown) prior to implantation in the vertebrae in which the helical spikes 550 and 552 do not have a conical shape, but instead have a generally cylindrical shape with a first maximum diameter. In addition, in the first condition, the helical spikes 550 and 552 have a first axial length. In order for the interbody stabilizer 920 to take the shape of the first condition, the temperature of the anchor must be below its TTR so that the material of the anchor is soft and ductile. As in the fourth embodiment of FIGS. 18–24, the interbody stabilizer 920 is also moved into the first condition with the aid of the tubular sleeve 70.

To return the helical spikes 550 and 552 to the conical shape as they emerge from the sleeve 70, heat is applied to the interbody stabilizer 920 until the temperature of the anchor exceeds the TTR for the shape memory material. With the helical spikes 550 and 552 expanding radially and contracting axially as they emerge from the sleeve 70, the helical spikes are implanted in a vertebrae in the conical shape, or second condition, as illustrated in FIG. 24C for the fourth embodiment. In the implanted second condition, the helical spikes 550 and 552 have a second maximum diameter that is larger than the first maximum diameter of the helical spikes in the first condition. Further, in the implanted second condition, the helical spikes 550 and 552 have a second axial length that is smaller than the first axial length of the helical spikes in the first condition.

One particular feature of the interbody stabilizer 920 is that the platform 924 is positioned in the intervertebral space between the adjacent vertebrae. This is possible because the helical spikes 550 and 552 project from the cylindrical side surface 932 of the platform 924. An advantage of the configuration according to the eighth embodiment is that the platform 924 becomes a wedge between the end plates of the vertebrae 912 and 914 and helps to maintain intervertebral spacing. Another advantage of the configuration according to the eighth embodiment is that the configuration leaves no part of the platform 932 extending outside of the vertebrae 912 and 914.

When implanted, the interbody stabilizer 920 is attached to both of the vertebrae 912 and 914 and securely fastens the vertebrae together. Because each of the helical spikes 550 and 552 penetrates into and subsequently out of each of the vertebrae 912 and 914, the helical spikes provide multiple fixation locations between the interbody stabilizer 920 and the vertebrae that pin the vertebrae together. The interbody stabilizer 920 is thus able to maintain proper intervertebral spacing and provide effective stabilization of the adjacent vertebrae 912 and 914, despite substantial forces on the interbody stabilizer caused by human body movement and muscle memory, while the bone graft material 590 fuses the vertebrae together. As mentioned previously, the conical shape of the helical spikes 550 and 552 increases the amount of surface area engaged by the interbody stabilizer 920, distributes any load on the interbody stabilizer, and provides fixation over a larger volume of bone. Finally, the use of a shape memory alloy for the helical spikes 550 and 552 allows the interbody stabilizer 920 to have a smaller diameter prior to implantation, which permits minimally invasive endoscopic surgery through a cannula, and a wider diameter when implanted, which improves fixation in the adjacent vertebrae 912 and 914.

Figure 41:
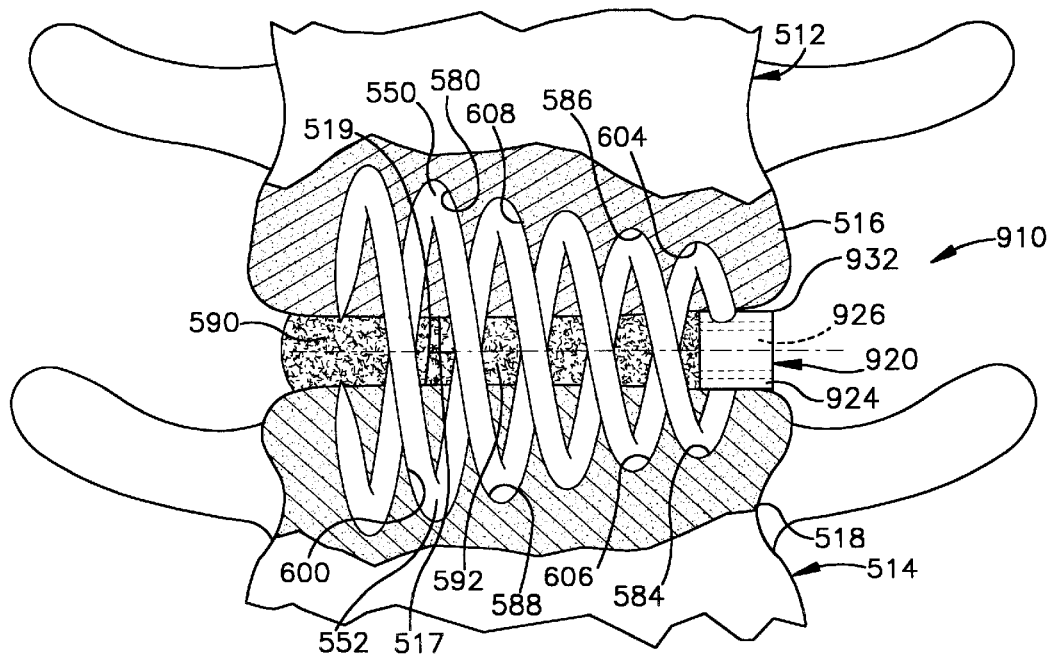
FIG. 41 is a view illustrating the apparatus of FIG. 39 implanted in an adjacent pair of lumbar vertebrae.

FIG. 41 illustrates the interbody stabilizer 920 of FIGS. 39 and 40 implanted in an adjacent pair of lumbar vertebrae, such as the lumbar vertebrae 512 and 514 shown in FIGS. 18 and 19. In FIG. 41, reference numbers that are the same as those used in the previous embodiments of FIGS. 18, 19, 39, and 40 designate parts that are the same as parts in the previous embodiments.

As discussed above with regard to FIGS. 39 and 40, a particular feature of the interbody stabilizer 920 is that the platform 924 is positioned in the intervertebral space between the adjacent vertebrae 512 and 514. This is possible because the helical spikes 550 and 552 project from the cylindrical side surface 932 of the platform 924. The advantage of this configuration is that the platform 924 becomes a wedge between the end plates of the vertebrae 512 and 514 and helps to maintain intervertebral spacing. Another advantage of this configuration is that no part of the platform 932 extends outside of the vertebrae 512 and 514.

When implanted, the interbody stabilizer 920 is attached to both of the vertebrae 512 and 514 and securely fastens the vertebrae together. Because each of the helical spikes 550 and 552 penetrates into and subsequently out of each of the vertebrae 512 and 514, the helical spikes provide multiple fixation locations between the interbody stabilizer 920 and the vertebrae that pin the vertebrae together. The interbody stabilizer 920 thus maintains proper intervertebral spacing and provides effective stabilization of the adjacent vertebrae 512 and 514, despite substantial forces on the interbody stabilizer caused by human body movement and muscle memory, while the bone graft material 590 fuses the vertebrae together. As mentioned previously, the conical shape of the helical spikes 550 and 552 increases the amount of surface area engaged by the interbody stabilizer 920, distributes any load on the interbody stabilizer, and provides fixation over a larger volume of bone. Finally, the use of a shape memory alloy for the helical spikes 550 and 552 allows the interbody stabilizer 920 to have a smaller diameter prior to implantation, which permits minimally invasive endoscopic surgery-through a cannula, and a wider diameter when implanted, which improves fixation in the adjacent vertebrae 512 and 514.

It should be noted that the interbody stabilizers described above can be used not only to stabilize a degenerative disc, but can also be used to correct spinal deformity such as scoliosis, kyphosis, lordosis, and spondylosisthesis.

Figure 44:
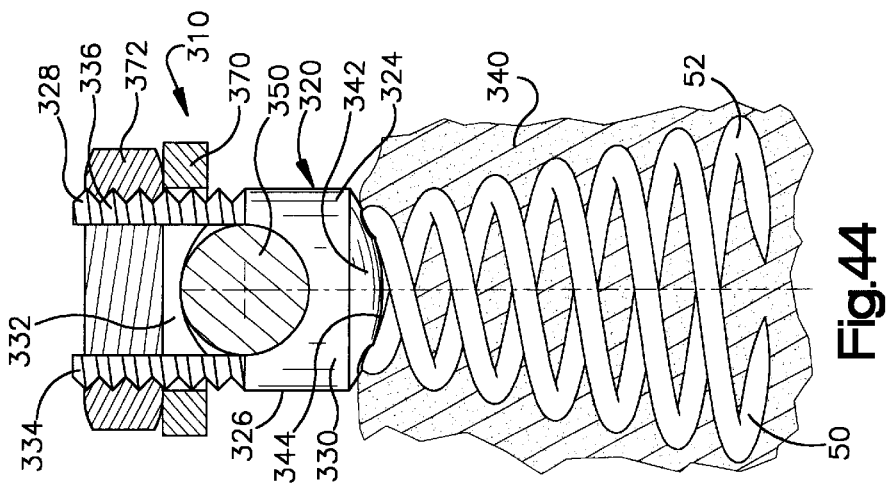
FIG. 44 is a sectional view taken along line 44—44 in FIG. 43.
Figure 43:
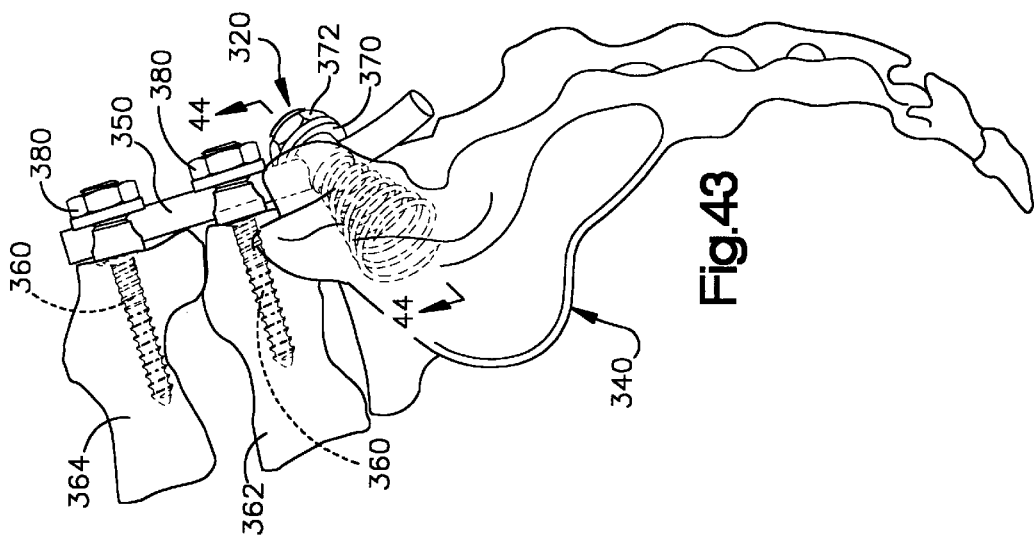
FIG. 43 is a side view of FIG. 42.
Figure 42:
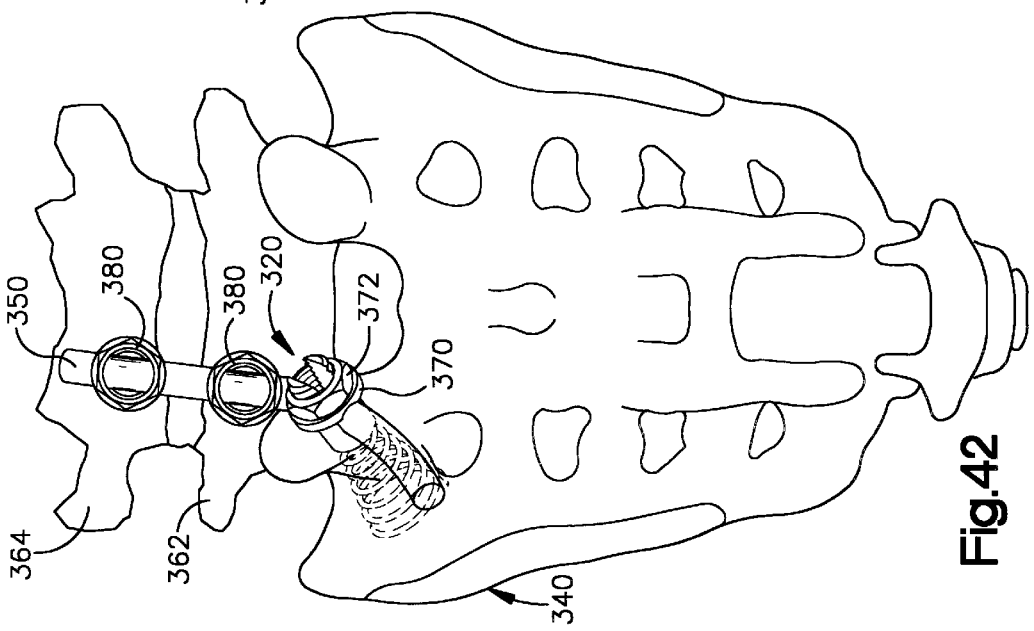
FIG. 42 is a schematic posterior view illustrating an apparatus constructed in accordance with a ninth embodiment of the present invention.

FIGS. 42–44 illustrate an apparatus 310 constructed in accordance with a ninth embodiment of the present invention. In the ninth embodiment of FIGS. 42–44, reference numbers that are the same as those used in the first embodiment of FIGS. 1–7 designate parts that are the same as parts in the fourth embodiment.

According to the ninth embodiment, the apparatus 310 comprises an anchor 320 implanted into a sacrum 340. The anchor 320 includes a platform 324 having a generally cylindrical outer surface 326 extending between oppositely disposed first and second ends 328 and 330. The platform 324 includes a slot 332 that extends axially from the first end 328 toward the second end 330 of the platform. Adjacent the first end 328, the outer surface of the platform 324 includes first and second segments of external threads 334 and 336 that are separated by the slot 332. The slot 332 and the threads 334 and 336 on the platform 324 provide structure for connecting a rod 350 to the anchor 320.

The second end 330 of the platform 324 includes an end surface 342 having a shape that is a complimentary to the shape of a surface 344 (FIG. 44) of the sacrum 340. The anchor 320 includes the first and second helical spikes 50 and 52, which are made from a shape metal alloy and previously described in detail with regard to the first embodiment of FIGS. 1–7. The helical spikes 50 and 52 extend from the end surface 342 of the platform 324.

The anchor 320 according to the ninth embodiment of FIGS. 42–44 is implanted in the sacrum 340 in much the same manner as the anchor 20 according to the first embodiment is implanted in the vertebrae 12. The shapes of the anchor 320 at various stages of the implantation process are similar to that which is illustrated in FIGS. 7A–7C for the anchor 20 of the first embodiment. Hence, the shape that is "memorized" into the material of the anchor 320 is best illustrated in FIG. 44. The anchor 320 has first and second conditions as described in the first embodiment, and utilizes the sleeve 70 to aid in moving the helical spikes 50 and 52 into the cylindrical first condition.

As shown in FIGS. 42 and 43, in addition to the anchor 320 being implanted in the sacrum 340, known screws 360 are implanted in the pedicles of lumbar vertebrae 362 and 364 above the sacrum. The rod 350 is then bent into a desired shape by the surgeon and placed into the slot 332 in the platform 324 of the anchor 320. A seat 370 is placed over the first end 328 of the platform 324 and engages the rod 350. A nut 372 screws down over the seat 370 and clamps the rod 350 to the anchor 320. In a similar fashion, the nuts 380 secure the rod 350 to the screws 360 implanted in the vertebrae 362 and 364 above the sacrum 340.

Because the helical spikes 50 and 52 of the anchor 320 displace less cancellous bone during implantation than a conventional solid shank bone screw, less torque is required to implant the anchor in the sacrum 340 than is required by a conventional bone screw. Further, the conical shape of the helical spikes 50 and 52 make the anchor 320 highly resistant to being pulled out of the sacrum 340 and to toggling in the sacrum despite being subjected to substantial forces caused by human body movement and muscle memory. As mentioned previously, the conical shape of the helical spikes 50 and 52 increases the amount of surface area engaged by the anchor 320, distributes any load on the anchor, and provides fixation over a larger volume of bone. Finally, the use of a shape memory alloy for the helical spikes 50 and 52 allows the anchor 320 to have a smaller diameter prior to implantation, which permits minimally invasive endoscopic surgery through a cannula, and a wider diameter when implanted, which improves fixation in the sacrum 340.

From the above description of the invention, those skilled in the art will perceive improvements, changes and modifications. It should be understood that the present invention can be used for a variety of purposes and can be implanted in other bones besides bones in the vertebrae column. Further, the present invention could be used to attach and stabilize other adjacent bones, not just bones in the spine or pelvis. It is further contemplated that the present invention could comprise a single helical spike, or more than three spikes. Such improvements, changes and modifications within the skill of the art are intended to be covered by the appended claims.

Having described the invention, I claim:

1. An apparatus for implanting into a bone in a patient's spine or pelvis, said apparatus, when implanted, being resistant to toggling in the bone and to being pulled from the bone, said apparatus comprising:

a platform for engaging a bone in a patient's spine or pelvis, said platform having a first surface that is solid and that extends generally transverse to a longitudinal axis of said apparatus, said platform including structure for connection to a spinal fixation implant; and at least one helical spike for embedding into the bone upon rotation of said platform, said at least one helical spike projecting tangentially from said first surface of said platform and extending around said longitudinal axis, said at least one helical spike having a tip portion at a distal end which penetrates into the bone as said platform is rotated;

said at least one helical spike, when implanted, having a conical shape that increases in diameter as said at least one helical spike extends away from said platform.

2. The apparatus of claim 1, wherein said at least one helical spike has a first condition in which said at least one helical spike has a first maximum diameter and a second condition in which at least a portion of said at least one helical spike expands to a second maximum diameter that is larger than said first maximum diameter.

3. The apparatus of claim 2 wherein said at least one helical spike has a first axial length in said first condition and a second axial length in said second condition, said second axial length being smaller than said first axial length.

4. The apparatus of claim 3 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

5. The apparatus of claim 4 wherein said at least one helical spike further has a connecting portion at a proximal end connected to said platform and an intermediate portion extending between said connecting portion and said tip portion, at least one of said intermediate portion and said tip portion being made of said shape memory alloy.

6. The apparatus of claim 5 comprising a pair of helical spikes extending around said longitudinal axis, said proximal ends of said pair of helical spikes being spaced 180° apart.

7. The apparatus of claim 5 comprising three helical spikes extending around said longitudinal axis, said proximal lends of said three helical spikes being spaced 120° apart.

8. The apparatus of claim 1 wherein said first surface has a shape that is complimentary to the shape of an outer surface of the bone for engaging the outer surface of the bone.

9. The apparatus of claim 1 wherein said at least one helical spike has a solid cross-section.

10. The apparatus of claim 1 wherein said at least one helical spike has a tubular cross-section.

11. The apparatus of claim 1 wherein a first portion of said at least one helical spike has a solid cross-section and a second portion of said at least one helical spike has a tubular cross-section.

12. An apparatus comprising:
at least one anchor for implantation into a bone, said at least one anchor having a longitudinal axis and, when implanted, being resistant to toggling in the bone and to being pulled from the bone; and
a spinal fixation implant for extending between and connecting a plurality of bones;
said at least one anchor including a platform having a first surface for facing the bone, said first surface being solid and extending generally transverse to said longitudinal axis, said platform further having structure for connection with said spinal fixation implant;
said at least one anchor further including at least two helical spikes for embedding into the bone upon rotation of said platform, said at least two helical spikes projecting tangentially from said first surface on said platform and extending around said longitudinal axis, each of said at least two helical spikes having a tip portion at a distal end which penetrates into the bone as said platform is rotated;
said at least two helical spikes, when implanted, having a conical shape that increases in diameter as said at least two helical spikes extend away from said platform.

13. The apparatus of claim 12 comprises a first anchor for implantation into a first bone and a second anchor for implantation into a second bone spaced from said first bone.

14. The apparatus of claim 13 wherein each of said first and second anchors extends co-linearly along said longitudinal axis, said at least two helical spikes that project from said first surface of said platform of said first anchor extending in a first direction, said at least two helical spikes that project from said first surface of said platform of said second anchor extending in a second direction opposite said first direction.

15. The apparatus of claim 14 wherein said spinal fixation implant comprises a member extending along said longitudinal axis and interconnecting said first and second anchors.

16. An apparatus for implantation into a bone in a patient's spine or pelvis, said apparatus, when implanted, being resistant to toggling in the bone and to being pulled from the bone, said apparatus comprising:
a platform for facing a bone in a patient's spine or pelvis, said platform having a first surface that is solid and that extends generally transverse to a longitudinal axis of said apparatus, said platform including structure for connection to a spinal fixation implant; and
at least one helical spike for embedding into the bone upon rotation of said platform, said at least one helical spike projecting tangentially from said first surface of said platform and extending around said longitudinal axis, said at least one helical spike having a tip portion at a distal end which penetrates into the bone as said platform is rotated;
said at least one helical spike having a first condition in which said at least one helical spike has a first maximum diameter and a second condition in which at least a portion of said at least one helical spike expands to a second maximum diameter that is larger than said first maximum diameter.

17. The apparatus of claim 16 wherein said at least one helical spike has a first axial length in said first condition land a second axial length in said second condition, said second axial length being smaller than said first axial length.

18. The apparatus of claim 17 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

19. The apparatus of claim 18 wherein said at least one helical spike, when implanted, has a conical shape that increases in diameter as said at least one helical spike extends away from said platform.

20. The apparatus of claim 19 wherein said at least one helical spike further has a connecting portion at a proximal end connected to said platform and an intermediate portion extending between said connection portion and said tip portion, at least one of said intermediate portion and said tip portion being made of said shape memory alloy.

21. The apparatus of claim 20 comprising a pair of helical spikes extending around said longitudinal axis, said proximal ends of said pair of helical spikes being spaced 180° apart.

22. The apparatus of claim 20 comprising three helical spikes extending around said longitudinal axis, said proximal ends of said three helical spikes being spaced 120° apart.

23. The apparatus of claim 16 wherein said first surface has a shape that is complimentary to the shape of an outer surface of the bone for engaging the outer surface of the bone.

24. An apparatus for implanting into a bone in a patient's spine or pelvis, said apparatus comprising:
- an anchor having a longitudinal axis, said anchor comprising a platform for facing the bone and at least one helical spike for embedding into the bone upon rotation of said platform;
- said platform having a first surface that is solid and that extends generally transverse to said longitudinal axis of said anchor, said platform including structure for connection to a spinal fixation implant;
- said at least one helical spike projecting tangentially from said first surface of said platform and extending around said longitudinal axis, said at least one helical spike having a tip portion at a distal end which penetrates into the bone as said platform is rotated;
- said at least one helical spike having a first condition in which said at least one helical spike has a first maximum diameter and a second condition in which at least a portion of said at least one helical spike expands to a second maximum diameter that is larger than said first maximum diameter;
- said anchor, when implanted, being resistant to toggling in the bone and to being pulled from the bone.

25. The apparatus of claim 24 further comprising a tubular sleeve for receiving said anchor, said tubular sleeve having an inside diameter that is approximately equal to said first maximum diameter of said at least one helical spike of said anchor, said anchor being positionable inside said tubular sleeve when in said first condition.

26. The apparatus of claim 25 wherein said tubular sleeve includes internal threads for mating with said at least one helical spike and helping to draw said at least one spike into said tubular sleeve as said platform is rotated.

27. The apparatus of claim 26 wherein said at least one helical spike has a first axial length in said first condition and a second axial length in said second condition, said second axial length being smaller than said first axial length.

28. The apparatus of claim 27 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

29. The apparatus of claim 28 wherein said at least one helical spike, when implanted, has a conical shape that increases in diameter as said at least one helical spike extends away from said platform.

30. An apparatus for implantation into a bone in a patient's spine or pelvis, said apparatus, when implanted, being resistant to toggling in the bone and to being pulled from the bone, said apparatus comprising:
- a platform for facing a bone in a patient's spine or pelvis, said platform having a first surface that is solid and that extends generally transverse to a longitudinal axis of said apparatus, said platform including structure for connection to a spinal fixation implant; and
- at least one helical spike for embedding into the bone upon rotation of said platform, said at least one helical spike projecting tangentially from said first surface of said platform and extending around said longitudinal axis, said at least one helical spike having a tip portion at a distal end which penetrates into the bone as said platform is rotated;
- said at least one helical spike having a first condition in which said at least one helical spike has a first axial length and a second condition in which said at least one helical spike has a second axial length that is smaller than said first axial length.

31. The apparatus of claim 30 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

32. The apparatus of claim 31 wherein said at least one helical spike, when implanted, has a conical shape that increases in diameter as said at least one helical spike extends away from said platform.

33. The apparatus of claim 32 wherein said at least one helical spike has a first maximum diameter in said first condition and at least a portion of said at least one helical spike expands to a second maximum diameter in said second condition, said second maximum diameter being larger than said first maximum diameter.

34. The apparatus of claim 33 wherein said at least one helical spike further has a connecting portion at a proximal end connected to said platform and an intermediate portion extending between said connecting portion and said tip portion, at least one of said intermediate portion and said tip portion being made of said shape memory alloy.

35. The apparatus of claim 34 comprising a pair of helical spikes extending around said longitudinal axis, said proximal ends of said pair of helical spikes being spaced 180° apart.

36. The apparatus of claim 34 comprising three helical spikes extending around said longitudinal axis, said proximal ends of said three helical spikes being spaced 120° apart.

37. The apparatus of claim 30 wherein said first surface has a shape that is complimentary to the shape of an outer surface of the bone for engaging the outer surface of the bone.

38. An apparatus for implantation into a bone in a patient's spine or pelvis, said apparatus, when implanted, being resistant to toggling in the bone and to being pulled from the bone, said apparatus comprising:
- a platform having a first surface for facing a bone in a patient's spine or pelvis, said platform having a first surface that is solid and that extends generally transverse to a longitudinal axis of said apparatus, said platform including structure for connection to a spinal fixation implant; and at least one helical spike for embedding into the bone upon rotation of said platform, said at least one helical spike projecting tangentially from said first surface of said platform and extending around said longitudinal axis, said at least one helical spike having a tip portion at a distal end which penetrates into the bone as said platform is rotated;

at least a portion of said at least one helical spike being made of a shape memory alloy that is responsive to changes in temperature above and below a predetermined temperature transition range, said at least one helical spike having a first shape when the temperature of said at least one helical spike is below said predetermined temperature transition range, said at least one helical spike having a second shape when heated above said predetermined temperature transition range, said at least one helical spike being implanted into the bone in said second shape.

39. The apparatus of claim 38 wherein said at least one helical spike, when implanted, has a conical shape that increases in diameter as said at least one helical spike extends away from said platform.

40. The apparatus of claim 39 wherein said at least one helical spike has a first axial length in said first shape and a second axial length in said second shape, said second axial length being smaller than said first axial length.

41. The apparatus of claim 40 wherein said at least one helical spike has a first maximum diameter in said first shape land at least a portion of said at least one helical spike expands to a second maximum diameter in said second shape, said second maximum diameter being larger than said first maximum diameter.

42. The apparatus of claim 38 wherein said at least one helical spike further has a connecting portion at a proximal end connected to said platform and an intermediate portion extending between said connecting portion and said tip portion, at least one of said intermediate portion and said tip portion being made of said shape memory alloy.

43. The apparatus of claim 42 comprising a pair of helical spikes extending around said longitudinal axis, said proximal ends of said pair of helical spikes being spaced 180° apart.

44. The apparatus of claim 42 comprising three helical spikes extending around said longitudinal axis, said proximal ends of said three helical spikes being spaced 120° apart.

45. The apparatus of claim 38 wherein said first surface has a shape that is complimentary to the shape of an outer surface of the bone for engaging the outer surface of the bone.

46. An apparatus for implantation into an adjacent pair of vertebral bodies having first and second surfaces that oppose each other, said apparatus, when implanted, being attached to each of the vertebral bodies and stabilizing the vertebral bodies while the vertebral bodies fuse together, said apparatus comprising:

a platform having a third surface extending generally transverse to a longitudinal axis of said apparatus; and at least one helical spike for embedding into each of the adjacent pair of vertebral bodies upon rotation of said platform to attach said at least one helical spike to each of the vertebral bodies and thus fasten the vertebral bodies together, said at least one helical spike projecting tangentially from said third surface of said platform and extending around said longitudinal axis, said at least one helical spike having a tip portion at a distal end for penetrating the first and second surfaces and for screwing into the adjacent pair of vertebral bodies as said platform is rotated;

said at least one helical spike at least partially defining an internal cavity for receiving material that promotes fusion of the vertebral bodies;

said at least one helical spike, when implanted, having a conical shape that increases in diameter as said at least one helical spike extends away from said platform.

47. The apparatus of claim 46 wherein said at least one helical spike has a first condition in which said at least one helical spike has a first maximum diameter and a second condition in which at least a portion of said at least one helical spike expands to a second maximum diameter that is larger than said first maximum diameter.

48. The apparatus of claim 47 wherein said at least one helical spike has a first axial length in said first condition and a second axial length in said second condition, said second axial length being smaller than said first axial length.

49. The apparatus of claim 48 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

50. The apparatus of claim 49 wherein said at least one helical spike further has a connecting portion at a proximal end connected to said platform and an intermediate portion extending between said connecting portion and said tip portion, at least one of said intermediate portion and said tip portion being made of said shape memory alloy.

51. The apparatus of claim 50 comprising a pair of helical spikes extending around said longitudinal axis, said proximal ends of said pair of helical spikes being spaced 180° apart.

52. The apparatus of claim 50 comprising three helical spikes extending around said longitudinal axis, said proximal ends of said three helical spikes being spaced 120° apart.

53. The apparatus of claim 46 wherein said at least one helical spike has a solid cross-section.

54. The apparatus of claim 46 wherein said at least one helical spike has a tubular cross-section.

55. The apparatus of claim 46 wherein a first portion of said at least one helical spike has a solid cross-section and a second portion of said at least one helical spike has a tubular cross-section.

56. An apparatus for implantation into an adjacent pair of vertebral bodies having first and second surfaces that oppose each other, said apparatus, when implanted, being attached to each of the vertebral bodies and stabilizing the vertebral bodies while the vertebral bodies fuse together, said apparatus comprising:

a platform having a third surface extending generally transverse to a longitudinal axis of said apparatus; and at least one helical spike for embedding into each of the adjacent pair of vertebral bodies upon rotation of said platform to attach said at least one helical spike to each of the vertebral bodies and thus fasten the vertebral bodies together, said at least one helical spike projecting tangentially from said third surface of said platform and extending around said longitudinal axis, said at least one helical spike having a tip portion at a distal end for penetrating the first and second surfaces and for screwing into the adjacent pair of vertebral bodies as said platform is rotated;

said at least one helical spike at least partially defining an internal cavity for receiving material that promotes fusion of the vertebral bodies;

said at least one helical spike having a first condition in which said at least one helical spike has a first maximum diameter and a second condition in which at least a portion of said at least one helical spike expands to a second maximum diameter that is larger than said first maximum diameter.

57. The apparatus of claim 56 wherein said at least one helical spike has a first axial length in said first condition and a second axial length in said second condition, said second axial length being smaller than said first axial length.

58. The apparatus of claim 57 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

59. The apparatus of claim 58 wherein said at least one helical spike, when implanted, has a conical shape that increases in diameter as said at least one helical spike extends away from said platform.

60. The apparatus of claim 59 wherein said at least one helical spike further has a connecting portion at a proximal end connected to said platform and an intermediate portion extending between said connecting portion and said tip portion, at least one of said intermediate portion and said tip portion being made of said shape memory alloy.

61. The apparatus of claim 59 comprising a pair of helical spikes extending around said longitudinal axis, said proximal ends of said pair of helical spikes being spaced 180° apart.

62. The apparatus of claim 59 comprising three helical spikes extending around said longitudinal axis, said proximal ends of said three helical spikes being spaced 120° apart.

63. An apparatus for implanting an interbody stabilizer into an adjacent pair of vertebral bodies having first and second surfaces that oppose each other, said apparatus comprising:

an interbody stabilizer having a longitudinal axis, said interbody stabilizer comprising a platform and at least one helical spike for embedding into each of the vertebral bodies upon rotation of said platform to attach said at least one helical spike to each of the vertebral bodies and thus fasten the vertebral bodies together;

a platform having a third surface extending generally transverse to said longitudinal axis;

said at least one helical spike projecting tangentially from said third surface of said platform and extending around said longitudinal axis, said at least one helical spike having a tip portion at a distal end for penetrating the first and second surfaces and for screwing into the adjacent pair of vertebral bodies as said platform is rotated;

said at least one helical spike at least partially defining an internal cavity for receiving material that promotes fusion of the vertebral bodies;

said at least one helical spike having a first condition in which said at least one helical spike has a first maximum diameter and a second condition in which at least a portion of said at least one helical spike expands to a second maximum diameter that is larger than said first maximum diameter;

said interbody stabilizer, when implanted, being attached to each of the vertebral bodies and stabilizing the vertebral bodies while the vertebral bodies fuse together.

64. The apparatus of claim 63 further comprising a tubular sleeve for receiving said interbody stabilizer, said tubular sleeve having an inside diameter that is approximately equal to said first maximum diameter of said at least one helical spike of said interbody stabilizer, said interbody stabilizer being positionable inside said tubular sleeve when in said first condition.

65. The apparatus of claim 64 wherein said tubular sleeve includes internal threads for mating with said at least one helical spike and helping to draw said at least one spike into said tubular sleeve as said platform is rotated.

66. The apparatus of claim 65 wherein said at least one helical spike has a first axial length in said first condition and a second axial length in said second condition, said second axial length being smaller than said first axial length.

67. The apparatus of claim 66 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

68. The apparatus of claim 67 wherein said at least one helical spike, when implanted, has a conical shape that increases in diameter as said at least one helical spike extends away from said platform.

69. An apparatus for implantation into an adjacent pair of vertebral bodies having first and second surfaces that oppose each other, said apparatus, when implanted, being attached to each of the vertebral bodies and stabilizing the vertebral bodies while the vertebral bodies fuse together, said apparatus comprising:

a platform having a third surface extending generally transverse to a longitudinal axis of said apparatus; and at least one helical spike for embedding into each of the adjacent pair of vertebral bodies upon rotation of said platform to attach said at least one helical spike to each of the vertebral bodies and thus fasten the vertebral bodies together, said at least one helical spike projecting tangentially from said third surface of said platform and extending around said longitudinal axis, said at least one helical spike having a tip portion at a distal end for penetrating the first and second surfaces and for screwing into the adjacent pair of vertebral bodies as said platform is rotated;

said at least one helical spike at least partially defining an internal cavity for receiving material that promotes fusion of the vertebral bodies;

said at least one helical spike having a first condition in which said at least one helical spike has a first axial length and a second condition in which said at least one helical spike has a second axial length that is smaller than said first axial length.

70. The apparatus of claim 69 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the bone in said second condition.

71. The apparatus of claim 70 wherein said at least one helical spike, when implanted, has a conical shape that increases in diameter as said at least one helical spike extends away from said platform.

72. The apparatus of claim 71 wherein said at least one helical spike has a first maximum diameter in said first condition and at least a portion of said at least one helical spike expands to a second maximum diameter in said second condition, said second maximum diameter being larger than said first maximum diameter.

73. The apparatus of claim 72 wherein said at least one helical spike further has a connecting portion at a proximal end connected to said platform and an intermediate portion extending between said connecting portion and said tip portion, at least one of said intermediate portion and said tip portion being made of said shape memory alloy.

74. The apparatus of claim 73 comprising a pair of helical spikes extending around said longitudinal axis, said proximal ends of said pair of helical spikes being spaced 180° apart.

75. The apparatus of claim 73 comprising three helical spikes extending around said longitudinal axis, said proximal ends of said three helical spikes being spaced 120° apart.

76. An apparatus for implantation into an adjacent pair of vertebral bodies having first and second surfaces that oppose each other, said apparatus, when implanted, being attached to each of the vertebral bodies and stabilizing the vertebral bodies while the vertebral bodies fuse together, said apparatus comprising:

a platform having a third surface extending generally transverse to a longitudinal axis of said apparatus; and at least one helical spike for embedding into each of the adjacent pair of vertebral bodies upon rotation of said platform to attach said at least one helical spike to each of the vertebral bodies and thus fasten the vertebral bodies together, said at least one helical spike projecting tangentially from said third surface of said platform and extending around said longitudinal axis, said at least one helical spike having a tip portion at a distal end for penetrating the first and second surfaces and for screwing into the adjacent pair of vertebral bodies as said platform is rotated;

said at least one helical spike at least partially defining an internal cavity for receiving material that promotes fusion of the vertebral bodies;

at least a portion of said at least one helical spike being made of a shape memory alloy that is responsive to changes in temperature above and below a predetermined temperature transition range, said at least one helical spike having a first shape when the temperature of said at least one helical spike is below said predetermined temperature transition range, said at least one helical spike having a second shape when heated above said predetermined temperature transition range, said at least one helical spike being implanted into the bone in said second shape.

77. The apparatus of claim 76 wherein said at least one helical spike, when implanted, has a conical shape that increases in diameter as said at least one helical spike extends away from said platform.

78. The apparatus of claim 77 wherein said at least one helical spike has a first axial length in said first shape and a second axial length in said second shape, said second axial length being smaller than said first axial length.

79. The apparatus of claim 78 wherein said at least one helical spike has a first maximum diameter in said first shape and at least a portion of said at least one helical spike expands to a second maximum diameter in said second shape, said second maximum diameter being larger than said first maximum diameter.

80. The apparatus of claim 79 wherein said at least one helical spike further has a connecting portion at a proximal end connected to said platform and an intermediate portion extending between said connecting portion and said tip portion, at least one of said intermediate portion and said tip portion being made of said shape memory alloy.

81. The apparatus of claim 80 comprising a pair of helical spikes extending around said longitudinal axis, said proximal ends of said pair of helical spikes being spaced 180° apart.

82. The apparatus of claim 80 comprising three helical spikes extending around said longitudinal axis, said proximal ends of said three helical spikes being spaced 120° apart.

* * * * *